(12) United States Patent
Hasegawa et al.

(10) Patent No.: US 10,399,999 B2
(45) Date of Patent: Sep. 3, 2019

(54) POLYMER COMPLEX AND PRODUCTION PROCESS THEREFOR

(71) Applicant: National University Corporation Hokkaido University, Sapporo-shi, Hokkaido (JP)

(72) Inventors: Yasuchika Hasegawa, Sapporo (JP); Ayako Nakajima, Sapporo (JP); Takayuki Nakanishi, Sapporo (JP); Yuichi Kitagawa, Sapporo (JP); Koji Fushimi, Sapporo (JP)

(73) Assignee: National University Corporation Hokkaido University, Sapporo-Shi, Hokkaido (JP)

( * ) Notice: Subject to any disclaimer, the term of this patent is extended or adjusted under 35 U.S.C. 154(b) by 18 days.

(21) Appl. No.: 15/556,855

(22) PCT Filed: Feb. 26, 2016

(86) PCT No.: PCT/JP2016/055906
§ 371 (c)(1),
(2) Date: Sep. 8, 2017

(87) PCT Pub. No.: WO2016/143561
PCT Pub. Date: Sep. 15, 2016

(65) Prior Publication Data
US 2018/0334472 A1    Nov. 22, 2018

(30) Foreign Application Priority Data

Mar. 9, 2015    (JP) ................................ 2015-045416

(51) Int. Cl.
*C07F 9/53*    (2006.01)
*C07C 49/92*   (2006.01)
*C09K 11/06*   (2006.01)

(52) U.S. Cl.
CPC ............ *C07F 9/5345* (2013.01); *C07C 49/92* (2013.01); *C09K 11/06* (2013.01); *C09K 2211/1433* (2013.01); *C09K 2211/182* (2013.01)

(58) Field of Classification Search
None
See application file for complete search history.

(56) References Cited

U.S. PATENT DOCUMENTS

2014/0287514 A1    9/2014    Humphrey et al.

FOREIGN PATENT DOCUMENTS

| JP | 3668966 B2 | 7/2005 |
| WO | 201215072 A1 | 2/2012 |
| WO | 2015002295 A1 | 1/2015 |
| WO | 2015119268 A1 | 8/2015 |

OTHER PUBLICATIONS

Miyata, et al., "Remarkable Luminescence Properties of Lanthanide Complexes with Asymmetric Dodecahedron Structures," Chem. Eur. J., 17, pp. 521-528 (2011).
Miyata, et al., "Thermostable Organo-phosphor: Low-Vibrational Coordination Polymers That Exhibit Different Intermolecular Interactions," ChemPlusChem., 77, 277-280 (2012).
Lee, et al., "Microporous Lanthanide-Organic Frameworks with Open Metal Sites: Unexpected Sorption Propensity and Multifunctional Properties," Inorganic Chemistry, vol. 49, pp. 4723-4725 (2010).
Lin, et al., "Microwave-Assisted Synthesis of a Series of Lanthanide Metal-Organic Frameworks and Gas Sorption properties," Inorganic Chemistry, vol. 51, pp. 1813-1820 (2012).
Ibarra, et al., "Gas Sorption and Luminescence Properties of a Terbium (III)—Phosphine Oxide Coordination Material with Two-Dimensional Pore Topology", Dalton Trans., vol. 41, pp. 8003-8009 (2012).
Ibarra, et al., "Molecular Sensing and Discrimination by a Luminescent Terbium—Phosphine Oxide Coordination Material", ChemComm, vol. 49, pp. 7156-7158 (2013).
Kuang, et al., "The Incorporation of the Quadruply Bonded Dimolybdenum (II) Unit Into an Unusual 2-D Polymeric Assembly Through the Use of the Asymmetric [4-Ph2P(O)C6H4CO2] Ligand That Provides Both Equatorial and Axial Donor Sites," Inorganic Chemistry Communications, vol. 5, pp. 134-138 (2002).
Miyata, et al., "Temperature-Dependent Luminescence of Lanthanide Coordination Polymers with Phosphine Oxide Ligands," pp. 59 (2012).
Gao, et al., "A Chiral Twofold Interpenetrated Diamond-Like 3D in (III) Coordination Network with 4,4',4"-Phosphoryltribenzoate," Inorganic Chemistry Communications, vol. 12, pp. 1238-1241 (2009).
Chen, et al., "Tailored Construction of Novel Nickel (II) and Manganese (II) Coordination Polymers Based on Tris(P-Carboxylpheny)Phosphine Oxide," Inorganica Chimica Acta, vol. 392, pp. 396-403 (2012).
Li, et al., "Construction of Two Microporous Metal—Organic Frameworks with Flu and Pyr Topologies Based on Zn4 (u3-OH)2(CO2)6 and Zn6(u6-O)(CO2)6 Secondary Building Units," Inorganic Chemistry, vol. 53, pp. 1032-1038 (2014).

(Continued)

*Primary Examiner* — Clinton A Brooks
(74) *Attorney, Agent, or Firm* — Panitch Schwarze Belisario & Nadel LLP

(57) ABSTRACT

Provided is an organic ligand capable of providing a complex that has a three-dimensional network structure due to rare-earth element ions. Also provided is a coordination polymer which includes this organic ligand, has a new function, and contains rare-earth element ions. Additionally, a process for producing the coordination polymer and a use of the coordination polymer are provided. In particular, provided is a coordination polymer having repeating units of formula (10):

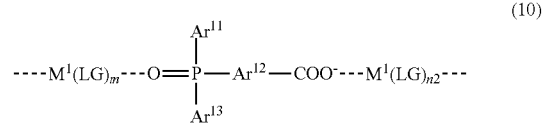

wherein each of the variable groups is as defined in the specification.

13 Claims, 13 Drawing Sheets

(56) References Cited

OTHER PUBLICATIONS

Morel, et al., "Synthesis and Characterication of Phosphine-Functionalized Metal-Organic Frameworks Based on MOF-5 and MIL-101 Topologies," Ind. Eng. Chem. Res., vol. 53, pp. 9120-9127 (2014).
Int'l Search Report and Written Opinion dated Apr. 26, 2016 in Int'l Application No. PCT/JP2016/055906.
Int'l Preliminary Report on Patentability dated Apr. 18, 2017 in Int'l Application No. PCT/JP2016/055906—Japanese Version.
Int'l Preliminary Report on Patentability dated Sep. 14, 2017 in Int'l Application No. PCT/JP2016/055906—English Version.

(A) SEM Image of Complex 1 (x200)

(B) SEM Image of Complex 1 (x2500)

(C) SEM Image of Complex 1 (x5000)

Tb: Large reduction of intensity
Eu: Increasing of intensity
(27-77 dergee Celsius)
and then small reduction of intensity Intensity ratio = $\dfrac{I_{Eu}}{I_{Tb}} = \dfrac{I_{613\,nm}}{I_{543\,nm}}$ ◎Luminescence dependent on temperature

POLYMER COMPLEX AND PRODUCTION PROCESS THEREFOR

CROSS-REFERENCE TO RELATED APPLICATION

This application is a Section 371 of International Application No. PCT/JP2016/055906, filed Feb. 26, 2016, which was published in the Japanese language on Sep. 15, 2016, under International Publication No. WO 2016/143561 A1, and the disclosure of which is incorporated herein by reference.

TECHNICAL FIELD

The present invention relates to a coordination polymer, a ligand for coordination polymer formation and a method of producing a coordination polymer. The coordination polymer is a complex which contains a rare earth element ion and with which an organic ligand coordinates. The present invention further relates to use of the coordination polymer of the present invention.

CROSS-REFERENCE TO RELATED APPLICATIONS

This application claims benefit of priority to Japanese Patent Application No. 2015-045416 filed on Mar. 9, 2015, which is expressly incorporated herein by reference in its entirety.

BACKGROUND ART

Rare earth complexes show sharp luminescence based on 4f-4f electronic transition, and thus recently attract the attention as novel luminescent materials. In addition, when rare earth complexes comprises organic ligands as a constituent, they exhibit compatibility with polymers and the like, and thus are proposed to be mixed with polymer materials and used as light-emitting devices or fluorescent inks. The rare earth complexes are also known to exhibit high heat resistance (PTL 1 and 2 and NPL 1).

Further, complex polymers which are polymerised due to a large number of coordination sites of complexes attract the attention as novel light-emitting materials. It has been reported that formation of coordination polymers by combining Eu(III) ions and aryl units can attain an improved thermostability and high emission quantum yield (NPL 2).
[PTL 1] WO 2012/15072
[PTL 2] Japanese Patent No. 3668966
PTL 1 and PTL 2 are expressly incorporated herein by reference in their entirety.
[NPL 1] K. Miyama, Y. Hasegawa et al, hem. Eur. J., 2011, 17, 521-528
[NPL 2] K. Miyata, T. Ohba et al, Chem Plus Chem., 2012, 77, 277
NPL 1 and NPL 2 are expressly incorporated herein by reference in their entirety

SUMMARY OF INVENTION

Technical Problem

Rare earth complexes have conventionally been developed by focusing on compatibility with polymers and the like and being luminescent substances having excellent heat resistance and some successful results have been attained. However, in order to achieve the practical use thereof in the fields of displays and luminescent printing, further improvement is required. Thus, there is a need for provision of a novel rare earth complex having heat resistance above 300° C. and excellent luminescence characteristics.

Thus, an object of the present invention is to provide a novel organic ligand which exhibits compatibility with polymers and the like and can provide a complex having a three-dimensional network structure due to a rare earth element ion, and a novel coordination polymer containing a rare earth element ion exhibiting a novel function (such as functions of luminescence, thermostability and electric property) with use of the organic ligand. Another object of the present invention is to provide a method of producing the coordination polymer and use of the coordination polymer.

Solution to Problem

The present invention is as set forth below.
[1] A complex comprising a repeating unit denoted by the following general formula (10):

[C1]

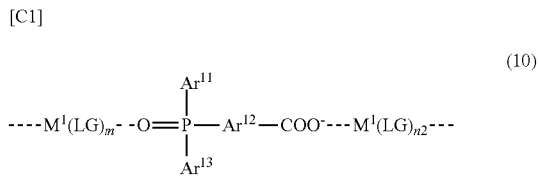

in the general formula (10):
$Ar^{11}$, $Ar^{12}$ and $Ar^{13}$ independently represent a substituted or unsubstituted aryl group, a substituted or unsubstituted heteroaryl group or a substituted or unsubstituted aralkyl group;
$M^1$ is a rare earth element ion;
LG is a multidentate ligand coordinating with the rare earth element ion denoted by $M^1$; m and n2 are arbitrary integers;
the symbol " . . . " at the terminal of "$M^1(LG)_m$ . . . " represents a bond to a phosphine oxide group in another repeating unit;
one or both of $Ar^{11}$ and $Ar^{13}$ are unsubstituted or respectively have at least one carboxyl group and have structures denoted by the following general formulae (11) and (12); n1 and n3 are arbitrary integers;
the symbol " . . . " in "$M^1(LG)_m$ . . . O=P" of the general formula (10) represents a bond between $M^1$ and O=P, " . . . " in "—COO⁻ . . . $M^1(LG)_{n2}$" represents a bond between —COO⁻ and $M^1$; and
the symbol " . . . " at the terminal of "$M^1(LG)_{n1-3}$" in the respective general formulae (10) to (12) represents a bond to a carboxyl group in another repeating unit;

[C2]

and

[2] The complex according to [1], wherein both $Ar^{11}$ and $Ar^{13}$ are unsubstituted.
[3] The complex according to [1], wherein both $Ar^{11}$ and $Ar^{13}$ have respectively at least one carboxyl group.
[4] The complex according to any one of [1] to [3], wherein the multidentate ligand LG is a diketonato compound.

[5] The complex according to [4], wherein the diketonato compound is denoted by the general formula (3):

[C3]

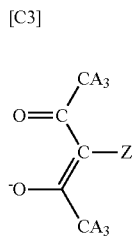
(3)

wherein each instance of A independently represents a hydrogen atom, a C1-6 alkyl group or a halogen atom; and Z represents a hydrogen atom or a deuterium atom.

[6] The coordination polymer according to [4] or [5], wherein the diketonato compound is at least one compound selected from the group consisting of acetyl acetone (acac), 2,2,6,6-tetramethylheptane-3,5-dione (TMHD), 1,1,1-trifluoroacetylacetone (TFA), 1,1,1,5,5,5-hexafluoroacetylacetone (HFA) and 1-(2-naphthyl)-4,4,4-trifluoro-1,3-butanedione.

[7] The coordination polymer according to any one of [1] to [6], wherein $M^1$ is at least two types of rare earth element ions.

[8] A ligand for a rare earth coordination polymer comprising a phosphine oxide compound denoted by the following general formula (1);

[C4]

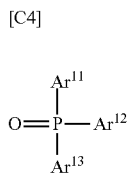
(1)

in the general formula (1):
$Ar^{11}$, $Ar^{12}$ and $Ar^{13}$ independently represent a substituted or unsubstituted aryl group, a substituted or unsubstituted heteroaryl group or a substituted or unsubstituted aralkyl group and at least one of $Ar^{11}$, $Ar^{12}$ and $Ar^{13}$ respectively has at least one carboxyl group.

[9] The ligand according to [8], wherein $Ar^{11}$, $Ar^{12}$ and $Ar^{13}$ independently represent a substituted or unsubstituted aryl group and at least one of $Ar^{11}$, $Ar^{12}$ and $Ar^{13}$ respectively has at least one carboxyl group.

[10] The ligand according to [8], wherein $Ar^{11}$, $Ar^{12}$ and $Ar^{13}$ independently represent a phenyl group and at least one of $Ar^{11}$, $Ar^{12}$ and $Ar^{13}$ respectively has at least one carboxyl group.

[11] A method of producing a coordination polymer, comprising a step of reacting the compound denoted by the general formula (1) according to any one of [8] to [10], a rare earth compound (provided that a rare earth ion in the rare earth compound is $M^1$) and a multidentate ligand LG to prepare a coordination polymer having a repeating unit denoted by the general formula (10) according to any one of [1] to [6].

Advantageous Effects of Invention

The present invention can provide a novel organic ligand, which exhibits compatibility with a polymer and the like and can provide a complex containing a new rare earth element ion having heat resistance. The present invention can further provide a novel coordination polymer which comprises the organic ligand and a rare earth element ion and achieves heat resistance. The present invention can further provide a method of producing the coordination polymer, a production intermediate of the coordination polymer and use of the coordination polymer. The production intermediate of the coordination polymer per se has luminescence function and can be applied to the applications similar to the coordination polymer.

DESCRIPTION OF EMBODIMENT

<Compound Denoted by General Formula (1)>

Figure 1:
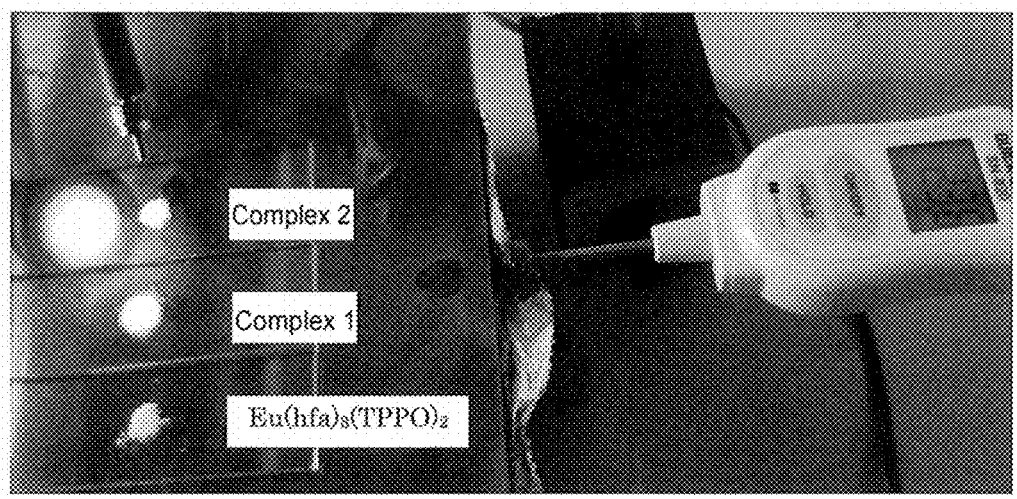
FIG. 1 shows an analytical device (status) by thermoluminescence analysis.

The present invention encompasses a phosphine oxide compound denoted by the following general formula (1), which can be used as a ligand in a coordination polymer comprising a rare earth element ion of the present invention.

[C5]

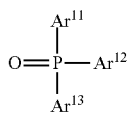

(1)

In the general formula (1), $Ar^{11}$, $Ar^{12}$ and $Ar^{13}$ independently represent a substituted or unsubstituted aryl group, a substituted or unsubstituted heteroaryl group or a substituted or unsubstituted aralkyl group and at least one of $Ar^{11}$, $Ar^{12}$ and $Ar^{13}$ respectively has at least one carboxyl group.

The aryl group in the optionally substituted aryl group is not specifically limited and examples thereof include a C6-20 aryl group. Examples of the C6-20 aryl group include phenyl, 1-naphthyl, 2-naphthyl, biphenylyl, anthryl and the like.

The substituent of the optionally substituted aryl group is not specifically limited and examples thereof include a C1-6 alkyl group, a C1-6 perfluoroalkyl group, a C6-14 aryl group, a 5- to 10-membered aromatic heterocyclic group, an alkoxy group, an aryloxy group, a siloxy group, a dialkylamino group and the like.

The C1-6 alkyl group, the C1-6 perfluoroalkyl group, the alkoxy group, the siloxy group and the dialkylamino group are described below.

Examples of the C1-6 alkyl group include methyl, ethyl, propyl, isopropyl, butyl, isobutyl, sec-butyl, tert-butyl, pentyl, hexyl and the like.

Examples of the C1-6 perfluoroalkyl group include trifluoromethyl, pentafluoroethyl, heptafluoropropyl, tridecafluorohexyl and the like.

Examples of the siloxy group include trimethylsiloxy, triethylsiloxy, triisopropylsiloxy, tert-butyldimethylsiloxy and the like.

Examples of the alkoxy group include a C1-6 alkoxy group. Examples of the C1-6 alkoxy group include a methoxy group, an ethoxy group, a hexyloxy group and the like. Examples of the dialkylamino group include dimethylamino, diethylamino and the like.

Examples of the C6-14 aryl group include phenyl, 1-naphthyl, 2-naphthyl, biphenylyl, 2-anthryl and the like. Examples of the 5- to 10-membered aromatic heterocyclic group include 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl and the like.

Examples of the aryloxy group include a C6-12 aryloxy group. Examples of the C6-12 aryloxy group include a phenoxy group, a naphthyloxy group and the like.

The position of substitution and the number of substituents as to the substituent in the optionally substituted aryl group are not specifically limited.

The heteroaryl group in the substituted or unsubstituted heteroaryl group is not specifically limited and examples thereof include an optionally condensed 5- to 14-membered aromatic heterocyclic group containing 1 to 3 atoms selected from a sulphur atom, an oxygen atom and a nitrogen atom.

Examples of the aromatic heterocyclic group include furyl, thienyl, pyrrolyl, pyrazolyl, imidazolyl, oxazolyl, isoxazolyl, isothiazolyl, thiazolyl, 1,2,3-oxadiazolyl, triazolyl, tetrazolyl, thiadiazolyl, pyridyl, pyridazinyl, pyrimidinyl, pyrazinyl, indolyl, indazolyl, purinyl, quinolyl, isoquinolyl, phthalazinyl, naphthylizinyl, quinoxalinyl, quinazolinyl, cinnolinyl, pteridinyl, carbazolyl, carbolinyl, phenanthridinyl, acridinyl and the like.

The substituent of the optionally substituted heteroaryl group may include those mentioned above for the optionally substituted aryl group.

The position of substitution and the number of substituents as to the substituent in the optionally substituted heteroaryl group are not specifically limited.

Examples of the aralkyl group in the optionally substituted aralkyl group include a benzyl group, a phenethyl group, a phenylpropyl group and the like.

The substituent of the optionally substituted aralkyl group may include those mentioned above for the optionally substituted aryl group.

The position of substitution and the number of substituents as to the substituent in the optionally substituted aralkyl group are not specifically limited.

$Ar^{11}$, $Ar^{12}$ and $Ar^{13}$ independently represent a substituted or unsubstituted aryl group and at least one of $Ar^{11}$, $Ar^{12}$ and $Ar^{13}$ may respectively have one carboxyl group. Further, $Ar^{11}$, $Ar^{12}$ and $Ar^{13}$ independently represent a phenyl group and at least one of $Ar^{11}$, $Ar^{12}$ and $Ar^{13}$ may respectively have one carboxyl group. The position of carboxyl group(s) and the number of substituents are not specifically limited; for example, when one carboxyl group exists, the carboxyl group may be at any of position 2, 3 or 4 and by taking the steric hindrance upon complex formation into account, the carboxyl group is preferably at, for example, position 4. When two carboxyl groups exist, the carboxyl groups may be at any of positions 2 and 4, 2 and 5, 2 and 6, 3 and 4 and 3 and 5, and by taking the steric hindrance upon complex formation into account, the carboxyl groups are preferably at, for example, positions 3 and 5. However, it is not intended to limit the present invention to the above.

<Method of Producing the Compound>

The compound denoted by the general formula (1) is, as exemplified in Examples, a phosphorus compound denoted by $P(Ar^{11}, Ar^{12}$ and $Ar^{13})$, and is obtained from a starting compound having an alkyl group at the Ar to which a carboxyl group is to sought to be introduced by oxidizing the alkyl group to a carboxyl group under oxidative conditions. The alkyl group at the Ar is preferably a methyl group because of the liability thereof to be oxidized to provide a carboxyl group. The oxidation reaction may be performed with an oxidizing agent such as potassium permanganate. The synthesised compound may be appropriately purified according to well-known methods.

<Coordination Polymer>

The present invention encompasses a coordination polymer comprising the compound of the present invention and a rare earth element ion.

The coordination polymer of the present invention has a repeating unit denoted by the following general formula (10):

[C6]

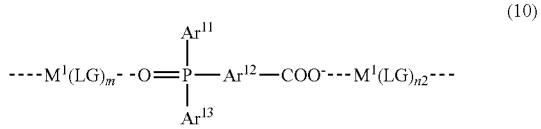
(10)

In the general formula (10), $Ar^{11}$, $Ar^{12}$ and $Ar^{13}$ independently represent, similar to those in the general formula (1), a substituted or unsubstituted aryl group, a substituted or unsubstituted heteroaryl group or a substituted or unsubstituted aralkyl group. The groups are used synonymously with the groups in the general formula (1).

$M^1$ is a rare earth element ion and, and a phosphine oxide group and/or a carboxyl group coordinates with the rare earth element ion $M^1$. It is predicted that the complex of the present invention comprises the rare earth element in the form of a rare earth element ion. The rare earth element may be one or more elements selected from the group consisting of, for example, Sc, Y, La, Ce, Pr, Nd, Pm, Sm, Eu, Gd, Tb, Dy, Tb, Dy, Ho, Er, Tm, Yb and Lu. The rare earth element ion is an ion having a valence intrinsic to the element and examples thereof include a cation having a valence of +2 or +3. From the view point of obtaining a luminescent substance, the rare earth element ion is preferably, for example, $Eu^{3+}$, $Tb^{3+}$, $Gd^{3+}$, $Tm^{3+}$ or $Er^{3+}$. When, for example, the rare earth element is $Eu^{3+}$, red luminescence is exhibited and when the rare earth element is $Tb^{3+}$, green luminescence is exhibited. The complex of the present invention encompasses complexes having single rare earth element and two or more types of rare earth elements.

LG is a multidentate ligand coordinating with the rare earth element ion denoted by $M^1$; and m and n2 are arbitrary integers.

The multidentate ligand denoted by LG is formed from a multidentate coordination compound and the multidentate coordination compound may be, for example, a bidentate compound, a tridentate compound or a tetradentate compound. Among the multidentate coordination compounds, examples of the bidentate compound include a diketonato compound and examples of the diketonato compound include a compound denoted by the general formula (3). In the general formula (3), each instance of A independently represents a hydrogen atom, a C1-6 alkyl group or a halogen atom, and Z represents a hydrogen atom or a deuterium atom. Examples of the C1-6 alkyl group include a methyl group, an ethyl group, a propyl group (n- and iso), a butyl group (n- and tert-), a pentyl group and a hexyl group.

[C7]

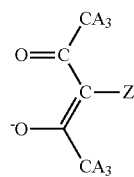
(3)

The diketonato compound denoted by the general formula (3) may be, more specifically, at least one compound selected from the group consisting of acetyl acetone (acac), 2,2,6,6-tetramethylheptane-3,5-dione (TMHD), 1,1,1-trifluoroacetylacetone (TFA), 1,1,1,5,5,5-hexafluoroacetylacetone (HFA) and 1-(2-naphthyl)-4,4,4-trifluoro-1,3-butanedione. The compounds are well known per se.

m and n2 are the coordination numbers of LG coordinating with the rare earth element ion $M^1$ and are arbitrary integers identified by the type of LG (the type and number of coordination position) and the valence of the rare earth element ion $M^1$. For example, m and n2 may be integers in the range of 1 to 10, such as 1, 2, 3, 4, 5, 6, 7, 8, 9 and 10.

The symbol "..." at the terminal of "$M^1(LG)_m$..." means a bond to a phosphine oxide group in another repeating unit denoted by the general formula (10). Another repeating unit denoted by the general formula (10) may have the same structure or a different structure. The symbol "..." in "$M^1(LG)_m$...O=P" of the general formula (10) denotes a bond between $M^1$ and O=P and the symbol "..." in "—COO⁻...$M^1(LG)_{n2}$" denotes a bond between —COO⁻ and $M^1$. All those bonds may be coordination bonds although it is not intended to limit the invention.

One or both of $Ar^{11}$ and $Ar^{13}$ are unsubstituted or respectively have at least one carboxyl group and have the structures denoted by the following general formulae (11) and (12). $M^1$ and LG are synonymous with those in the general formula (10). n1 and n3 are, similar to n2, coordination numbers of the LG coordinating with the rare earth element ion $M^1$ and are arbitrary integers identified by the type of LG (the type and number of coordination position) and the valence of the rare earth element ion $M^1$. For example, n1 and n3 may be integers in the range of 1 to 10, such as 1, 2, 3, 4, 5, 6, 7, 8, 9 and 10.

[C8]

(11)

(12)

The symbol "..." at the terminal of "$M^1(LG)_{n1-3}$..." in the general formulae (10) to (12) represents a bond to a carboxyl group in another repeating unit denoted by the general formula (10).

Both $Ar^{11}$ and $Ar^{13}$ may be unsubstituted or both $Ar^{11}$ and $Ar^{13}$ may respectively have one carboxyl group.

A putative structural formula of the coordination polymer in which all $Ar^{11}$, $Ar^{12}$ and $Ar^{13}$ are phenyl groups, both $Ar^{11}$ and $Ar^{13}$ are unsubstituted (the compound of the general formula (1) has one carboxyl group), $M^1$ is Eu and LG is 1,1,1,5,5,5-hexafluoroacetylacetone (HFA) is shown below. The following structural formula comprises three compounds of the general formula (1), in which Eu on left coordinates with phosphine oxide groups from two compounds of the general formula (1) and three HFA moieties and Eu on right coordinates with carboxyl groups from two compounds of the general formula (1), one HFA moiety and two water molecules. The carboxyl group on the left terminal and the phosphine oxide group on the right terminal are represented as in free form; however, the groups respectively coordinate with Eu, although it is not indicated. The actual coordination polymer is a linear coordination polymer comprising more than one repeating unit denoted by the structural formula and at the termini, the carboxyl group and the phosphine oxide group may be in free form.

[C9]

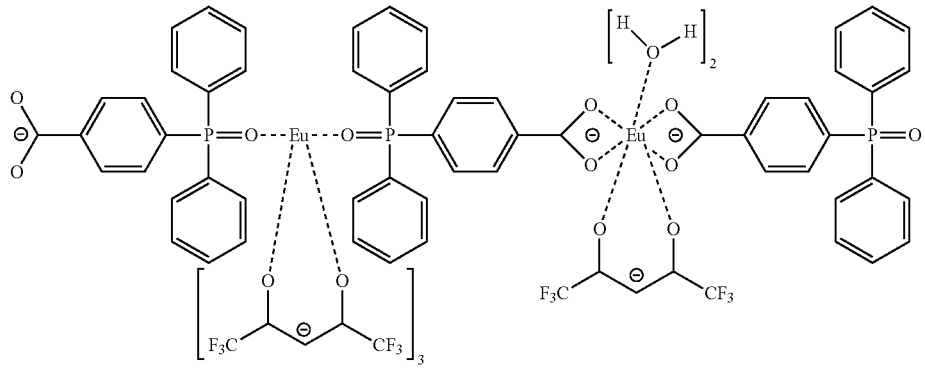

A putative structural formula of the coordination polymer in which all $Ar^{11}$, $Ar^{12}$ and $Ar^{13}$ are phenyl groups, both $Ar^{11}$ and $Ar^{13}$ have carboxyl groups (the compound of the general formula (1) has three carboxyl groups), $M^1$ is Eu and LG is 1,1,1,5,5,5-hexafluoroacetylacetone (HFA) is shown below. The following structural formula comprises four compounds of the general formula (1), in which Eu on left coordinates with phosphine oxide groups from two compounds of the general formula (1) and three HFA moieties. Eu on upper right coordinates with carboxyl groups from three compounds of the general formula (1) and two water molecules. Eu on lower right coordinates with carboxyl groups from two compounds of the general formula (1). Although it is not indicated, the latter Eu may coordinate with a carboxyl group of another compound of the general formula (1) and 2 water molecules or one HFA moiety and two water molecules. The carboxyl groups and the phosphine oxide groups represented as in free form respectively coordinate with Eu, although it is not indicated. The actual coordination polymer is a three-dimensionally crosslinked coordination polymer comprising more than one repeating unit denoted by the structural formula. At the termini, the carboxyl groups and the phosphine oxide groups may be in free form. A three-dimensionally crosslinked coordination polymer tends to have higher heat resistance than a linear coordination polymer, provided that the coordination polymers have the same constituents.

[C10]

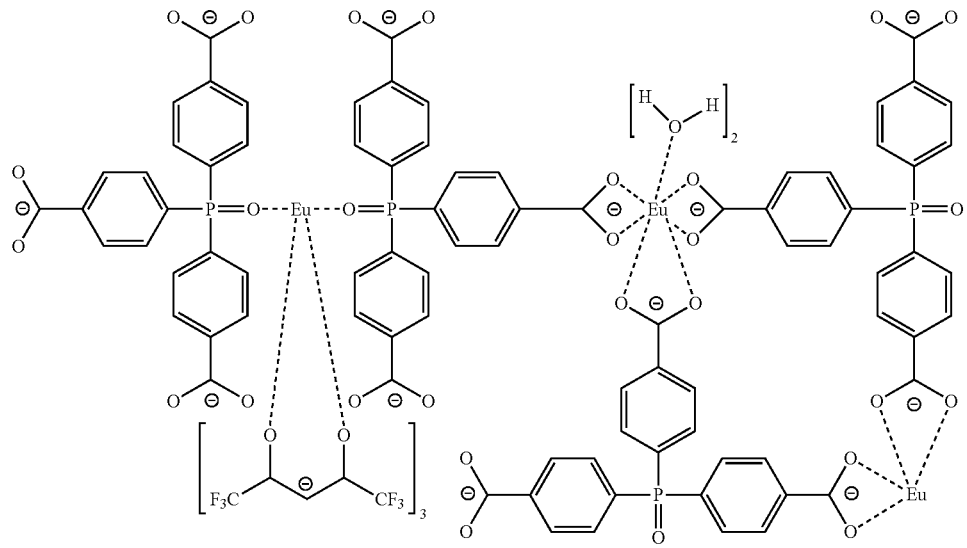

A putative structural formula of the coordination polymer in which all $Ar^{11}$, $Ar^{12}$ and $Ar^{13}$ are phenyl groups, both $Ar^{11}$ and $Ar^{13}$ have carboxyl groups (the compound of the general formula (1) has three carboxyl groups), $M^1$ is Eu and Tb and LG is 1,1,1,5,5,5-hexafluoroacetylacetone (HFA) is shown below. The following structural formula comprises four compounds of the general formula (1), in which Eu on left coordinates with phosphine oxide groups from two compounds of the general formula (1) and three HFA moieties. Tb on upper right coordinates with carboxyl groups from three compounds of the general formula (1) and two water molecules. Eu on lower right coordinates with carboxyl groups from two compounds of the general formula (1). Although it is not indicated, the latter Eu may coordinate with a carboxyl group of one more compound of the general formula (1) and two water molecules or one HFA moiety and two water molecules. The carboxyl groups and the phosphine oxide groups represented as in free form respectively coordinate with Eu, although it is not indicated.

The positions of Eu and Tb are arbitrary. Tb may be positioned at the position of Eu on left, Eu may be positioned at the position of Tb on upper right, and Tb may be positioned at the position of Eu on lower right. Depending on the ratio of Eu to Tb, the number of Eu and Tb existing in the unit denoted by the structural formula varies, and in some cases, a unit in which one of Eu and Tb is absent (a unit wherein $M^1$ is only Eu or only Tb) and a unit in which Eu and Tb coexist may coexist. The actual coordination polymer is a three-dimensionally crosslinked coordination polymer comprising more than one type of repeating units denoted by the structural formula. At the termini, the carboxyl groups and the phosphine oxide groups may be in free form. A three-dimensionally crosslinked coordination polymer tends to have higher heat resistance than a linear coordination polymer, provided that the coordination polymers have the same constituents. As described above, in a complex comprising $M^1$ which is more than one type of rare earth element ions such as Eu and Tb exhibiting different responses to the temperature, luminescent colour may change depending on the temperature.

to 10,000, in the range of 2 to 1,000, in the range of 2 to 500 or in the range of 3 to 300. The coordination polymer of the present invention is usually a mixture of more than one complex having different repetition numbers. In case of the mixture, the repetition number means an average of the repetition numbers of the complexes in the mixture.

<Method of Producing the Coordination Polymer>

The coordination polymer of the present invention may be produced by, for example, a method comprising a step for reacting the compound denoted by the general formula (1), a rare earth compound (provided that the rare earth compound comprises the rare earth ion $M^1$) and a multidentate ligand LG to prepare the coordination polymer having a repeating unit denoted by the general formula (10).

A compound denoted by the general formula (1), a rare earth element-containing compound and a multidentate ligand LG are mixed in a solvent to obtain a complex of the compound, the rare earth element and the multidentate ligand LG. The mixing ratio between the compound denoted by the general formula (1), the rare earth element-containing compound and the multidentate ligand LG may be appropriately selected according to the types of the compound denoted by the general formula (1), the rare earth element

[C11]

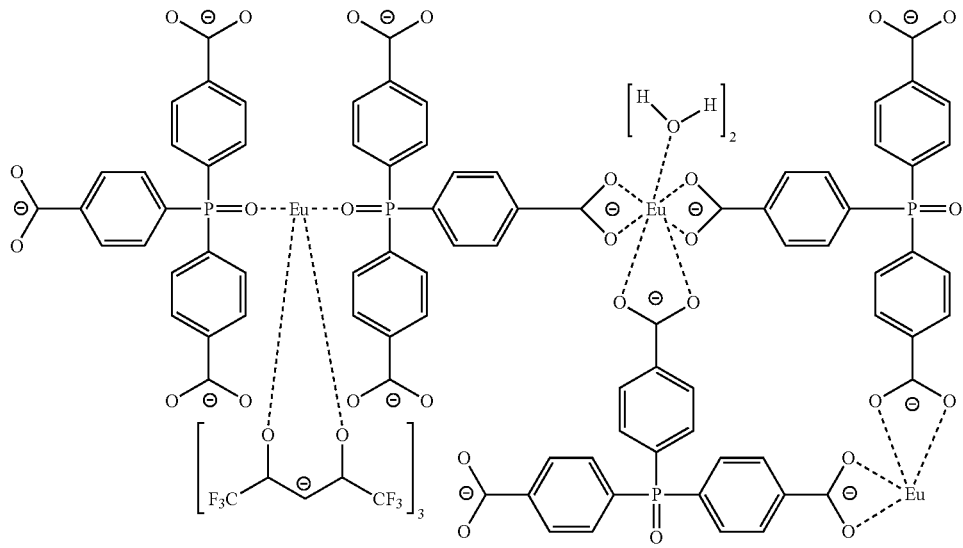

The repetition number of the repeating unit denoted by the general formula (10) in the coordination polymer of the present invention may be, for example, in the range of 2 to 500,000. In view of the properties desired for the coordination polymer of the present invention, the repetition number may be appropriately selected within the range. The repetition number may be appropriately adjusted by adjusting the production method and conditions thereof, the type of the rare earth metal ion and the type of $Ar^{11}$, $Ar^{12}$ and $Ar^{13}$. A coordination polymer having an increased molecular weight tends to have excellent heat resistance, while an increase in the molecular weight tends to cause less admixture with or dispersion in another material. In view of the above as well as of the type of constituents, the repetition number may be appropriately selected. The repetition number may be, depending on the application thereof or the type of the constituting ligand or the type of the rare earth element ion, in the range of, for example, 2 to 100,000, in the range of 2 ion and the multidentate ligand LG. Particularly, by taking the number of carboxyl groups in the compound denoted by the general formula (1) into account, (the number of moles of the compound denoted by the general formula (1)/the number of moles of the rare earth element) may be, for example, in the range of 0.5 to 10, preferably in the range of 0.5 to 5 and more preferably in the range of 1 to 3. (The number of moles of the multidentate ligand LG/the number of moles of the rare earth element) may be, for example, in the range of 0.5 to 10, preferably in the range of 0.5 to 8 and more preferably in the range of 1 to 5.

The solvent used is one that can dissolve both the compound of the present invention and the rare earth element-containing compound. For example, without limitation, methanol, ethanol, acetone, toluene, chloroform, dichloromethane, dichloroethane, pyridine, DMSO (dimethyl sulphoxide), DMF (dimethylformamide) and the like may be used. Mixing in the solvent may be carried out in the range of, for example, from room temperature (for example, 20° C.) to 120° C. The temperature may be appropriately selected by taking the boiling point of the solvent used into account. In view of promoting the reaction, the reaction is preferably carried out under heating and the temperature may be, for example, 40° C. or higher or 50° C. or higher and at or lower than the boiling point of the solvent. The reaction time may be appropriately selected by taking the starting materials and the reaction conditions and the yield of the product into account. The reaction time may be in the range of 1 minute to 100 hours. It is not intended that the invention is limited to the above ranges.

The rare earth element-containing compound used for the reaction is not specifically limited as far as the compound contains a rare earth element. The rare earth element-containing compound may be, for example, a coordination compound and a rare earth element ion-containing compound. The coordination compound and the rare earth element ion-containing compound may be, for example, a rare earth element ion complex compound comprising a coordination compound as at least some of the ligands. The rare earth element ion complex compound comprising a coordination compound as some of the ligands and the rest of the ligands which have lower coordination power than the coordination power of the compound denoted by the general formula (1) towards the rare earth element ion is preferable in view of facilitating the synthesis of the rare earth complex of the general formula (10). Examples of the ligand having lower coordination power than the coordination power of the compound denoted by the general formula (1) towards the rare earth element ion include water ($H_2O$), methanol, ethanol and the like. The generated coordination polymer of the present invention may be purified according to standard methods.

<Light-Emitting Elements>

The present invention covers light-emitting elements employing the complex of the present invention as a light-emitting material. The light-emitting element of the present invention can comprise a thin film of the complex of the present invention. More specifically, the coordination polymer of the present invention can be employed, for example, in the light-emitting layer (light-emitting medium) of a white LED element and in the light-emitting layer of an organic electroluminescent element. The light-emitting element of the present invention can also be used in display and illumination. The coordination polymer of the present invention can also be used, for example, in fluorescent ink compositions.

When employing the coordination polymer in these applications, a single type of the coordination polymer can be employed, or two or more types can be combined for use.

The coordination polymer can be employed in mixtures where it is incorporated as an essential component and other ions, compounds, and the like are additionally incorporated. It suffices for the coordination polymer to be incorporated into such mixtures; to the extent that the effect of the present invention is not compromised, rare earth metal ions, coordination polymers not coordinated with the compound of the present invention, and the like can be further incorporated.

(1) The White LED Element

The same configurations as in known LED elements can be adopted in the white LED element of the present invention, with the exception that the above coordination polymer is incorporated into the light-emitting medium (fluorescent material) constituting the light-emitting layer. Examples are LED elements having light-emitting layers comprised of LED chips and light-emitting media.

In LED chips, electric energy is received by an electrode, and light is generated and released. A light-emitting medium (fluorescent material) that absorbs light emitted by an LED chip releases light of a different wavelength from the light absorbed. At that time, by combining the light that is released by the LED chip with light released by a fluorescent material, it is possible to create a new color of light. In the present invention, it is possible to emit white light by incorporating the above coordination polymer into a fluorescent material. The coordination polymer can be suitably dissolved in an organic medium. Since it will essentially not precipitate out of an organic medium, white light can be released with high efficiency (at a high light extraction efficiency).

It suffices for the LED chip to be an element that releases light in the ultraviolet to near ultraviolet to visible to near infrared region; there is no specific limitation. Examples are blue LEDs and near ultraviolet LEDs.

The light-emitting medium is obtained by dissolving the coordination polymer in an organic medium. In the present invention, it is possible to control the color emitted by the light-emitting medium by suitably selecting the rare earth element ions (central element ions) in the coordination polymer. For example, in a light-emitting medium containing a coordination polymer in which all of the central element ions are $Eu^{3+}$, red light can be emitted. Further, a light-emitting medium containing a coordination polymer in which all of the central element ions are $Tb^{3+}$ will emit green light. Still further, a light-emitting medium containing a coordination polymer in which the central element ions are rare earth element ions other than $Eu^{3+}$ and $Tb^{3+}$ (for example, where all of the central element ions are $Tm^{3+}$) will emit blue light.

Two or more of the coordination polymers set forth above can be incorporated into the light-emitting medium. From the perspective of lowering the light extraction efficiency and the like, it is better not to incorporate particles of known fluorescent inorganic compounds into the light-emitting medium. However, to the extent that the effect of the present invention is not impeded, these particles can be incorporated as needed.

Examples of the above particles are yellow light-emitting inorganic compound particles that function by activating $Y_3Al_5O_{12}$ (YAG) with Ce; blue light-emitting inorganic compound particles such as particles that function by activating $Sr_{10}(PO_4)_6Cl_2$ with Eu, particles that function by activating $Ca_{10}(PO_4)_6C_{12}$ with Eu, particles that function by activating $Ba_{10}(PO_4)_6C_{12}$ with Eu, particles that function by activating $BaMgAl_{10}O_{17}$ with Eu, and particles that function by activating $Ba_3MgSi_2O_8$ with Eu; inorganic compound particles emitting green light such as particles that function by activating $SrGa_2S_4$ with Eu, particles that function by activating $CaAl_2O_4$ with Eu, particles that function by activating $BaAl_2O_4$ with Eu, and particles that function by activating $SrAl_2O_4$ with Eu; and inorganic compound particles that emit red light such as particles that function by activating SrS with Eu, particles that function by activating CaS with Eu, particles that function by activating $CaAlSiN_3$ with Eu, and particles that function by activating $Ba_3MgSi_2O_8$ with Eu or Mn. These particles can be employed singly, or in combinations of two or more.

For example, when the following LED chips are combined with a light-emitting medium, suitable white light can be obtained:

(1) LED chip: Blue LED (such as InGaN); light-emitting medium: red light-emitting coordination polymer+yellow light-emitting inorganic compound particle (such as particles that function by activating $Y_3Al_5O_{12}$ (YAG) crystals with Ce)

(2) LED chip: Blue LED (such as InGaN); light-emitting medium: red light-emitting coordination polymer+green light-emitting coordination polymer (3) LED chip: near ultraviolet LED (such as InGaN); light-emitting medium: blue light-emitting inorganic compound particle (such as particles that function by activating $Sr_{10}(PO_4)_6Cl_2$ with Eu, particles that function by activating $Ca_{10}(PO_4)_6Cl_2$ with Eu, and particles that function by activating $Ba_{10}(PO_4)_6C_{12}$) with Eu+red light-emitting coordination polymer+green light-emitting coordination polymer (4) LED chip: near ultraviolet LED (such as InGaN); light-emitting medium: red light-emitting coordination polymer+green light-emitting coordination polymer+blue light-emitting coordination polymer Examples of the above organic media are organic solvents and liquid polymers.

Examples of the above organic solvents are fluorine-based solvents. These organic solvents can be employed singly or as mixtures comprised of two or more solvents.

Examples of the liquid polymer are fluororesins and silicone resins. The fluororesins and silicone resins can be employed in the form of suitable commercial products. Examples of commercial products of fluororesins are Teflon (registered trademark) AF (made by Dupont) and Cytop (made by Asahi Glass). Examples of commercial products of silicone resins are polydimethyl siloxane, polymethylphenyl siloxane, polydiphenyl siloxane and the like.

In particular, liquid polymers are desirable and fluororesins are preferred as organic media. Fluororesins have characteristics such as a high glass transition point, high moisture resistance, and low gas permeability. Thus, the use of a fluororesin as the organic medium enhances the light-emitting characteristics, emission lifetime, durability, and the like of light-emitting medium.

The content of the coordination polymer in the light-emitting medium is not specifically limited; about 5 to 90 mass % is desirable.

The content of the fluorescent inorganic compound particles in the light-emitting medium is not specifically limited so long as it does not impede the present invention.

The white LED element of the present invention can be used in various LEDs such as bullet-type LEDs and surface-mounted LEDs. The same configuration as that of known LEDs can be adopted as the specific configuration of the LED with the exception that the above white LED element is utilized.

(2) Organic Electroluminescent (EL) Element

The organic EL element of the present invention comprises a light-emitting layer comprising the above mentioned coordination polymer.

Organic electroluminescent elements normally have a configuration comprised of, sequentially layered on a substrate, an anode, a charge (hole) transport layer, the light-emitting layer, a charge (electron) transport layer, and a cathode. The content of the coordination polymer in the light-emitting layer can be, for example, about 5 to 100 mass %.

The light-emitting layer can be formed solely of the coordination polymer of the present invention, or can contain other compounds in addition to the coordination polymer of the present invention. For example, it can contain the charge (hole) transport layer material or the charge (electron) transport layer material described below as a host compound.

The thickness of the light-emitting layer must be at least adequate to prevent the formation of pinholes. Excessive thickness is undesirable in that the resistance of the element increases and a high drive voltage becomes necessary. Accordingly, the thickness of the light-emitting layer is about 0.0005 to 10 µm, desirably about 0.001 to 1 µm, and preferably, about 0.005 to 0.2 µm.

The method of forming the light-emitting layer is not specifically limited. Examples are the method of vapor depositing the coordination polymer on the hole transport layer, or methods of coating the luminescent ink composition described farther below such as the spin coating method or printing methods such as the ink jet method.

It suffices for the substrate to be transparent. Examples are glass, quartz, and optically transparent plastic films (polyethylene terephthalate (PET), polyethylene naphthalate (PEN), polyether sulfone (PES), polyetherimide, polycarbonate (PC), and the like). The thickness of the substrate is not specifically limited so long as it does not impede the effect of the present invention.

By way of example, indium tin oxide (ITO), which is an electrically conductive material with a high work function, can be employed as the anode material. The thickness of the anode can be about 0.1 to 0.3 µm.

By way of example, an arylamine compound such as triarylamine can be employed as the material of the charge (hole) transport layer. One such material, or a combination of two or more such materials, can be employed.

By way of example, tris(8-hydroxyquinolinol)aluminum, triazoles, phenanthrolines, and oxadiazoles can be employed as the materials of the charge (electron) transport layer. One such material, or a combination of two or more such materials, can be employed.

The thickness of each of these charge transport layers is normally about 0.0005 µm to 10 µm, desirably about 0.001 to 1 µm.

A metal with a low work function such as aluminum, magnesium, indium, aluminum-lithium alloy, or magnesium-silver alloy can be used as the cathode material. The thickness of the cathode is desirably about 0.01 to 0.5 µm.

The anode, hole transport layer, electron transport layer, and cathode can be formed by known methods such as resistance heating vapor deposition, vacuum vapor deposition, or sputtering employing the various above materials.

The organic EL element of the present invention can be employed as an illuminator such as the backlight of a color liquid-crystal display device, as a display, or the like.

(3) The Luminescent Ink Composition

The luminescent ink composition of the present invention contains the above coordination polymer. The light emitted by the coordination polymer in natural lighting is essentially colorless.

When the coordination polymer is irradiated with ultraviolet light, the complex emits colored light, making it possible to observe the light emitted. Accordingly, an ink composition in which the coordination polymer has been dissolved can be printed on various substrates to permit viewing of the printed contents only when irradiated with ultraviolet light employing a black light or the like. For example, the ink composition can be printed on substrates such as paper bills, documents, publications, and cards to impart a security function of preventing forgery, unauthorized copying, and the like.

The color of the light emitted varies with the type of the central element ion of the coordination polymer. For example, when the central element ion is $Eu^{3+}$, the complex will emit an intensely red light. When the central element ion is $Tb^{3+}$, the complex will emit intense green light. When multiple central element ions are present in the coordination polymer, the multiple rare earth element ions are desirably all identical.

Two or more types of coordination polymer compositions can be incorporated into the above ink composition.

For example, it is possible to prepare a two-color mixture-type ink by mixing a first fluorescent material in the form of the coordination polymer of the present invention comprised of a central element ion in the form of $Tb^{3+}$ that emits intense green light when irradiated with a black light lamp emitting ultraviolet radiation in wavelengths of 365 nm and 254 nm and a second fluorescent material in the form of the coordination polymer of the present invention comprised of a central element ion in the form of $Eu^{3+}$ that emits almost no red light when irradiated with a black light-emitting ultraviolet radiation with a wavelength of 254 nm but emits intense red light when irradiated with a black light lamp emitting ultraviolet radiation with a wavelength of 365 nm.

When the above ink composition is irradiated with a black light lamp emitting ultraviolet radiation with a wavelength of 365 nm, the first and second fluorescent materials emit a color close to yellow by emitting a mixture of green and red. When irradiated with a black light lamp emitting ultraviolet radiation with a wavelength of 254 nm, the second fluorescent material emits almost no light, so just the green of the first fluorescent material is emitted.

Since differing hues can be distinguished using the two wavelength regions in this manner, it is easier to distinguish between forgeries and authentic items.

The content of the coordination polymer in the fluorescent ink composition of the present invention can be suitably set based on the type of substrate or the like. A content of about 0.001 to 30 mass % is desirable, and about 0.05 to 3 mass % is preferred.

Additives such as solvents, resins (binders), penetrating agents, defoamers, dispersing agents, and colorants can be incorporated as needed into the fluorescent ink composition of the present invention. In particular, in the ink composition of the present invention, the coordination polymer is desirably dissolved in a solvent.

Solvents capable of dissolving the coordination polymer can be employed as this solvent. Examples are ketone solvents such as acetone, methyl ethyl ketone, and cyclohexanone; aliphatic hydrocarbon solvents such as n-hexane, cyclohexane, n-pentane, and n-heptane; aromatic hydrocarbon solvents such as toluene and xylene; ether solvents such as tetrahydrofuran, 1,4-dioxane, methyl cellosolve, ethyl cellosolve, butyl cellosolve, diethylene glycol monobutyl ether, and ethylene glycol monobutyl ether; alcohol solvents such as methanol, ethanol, propanol, isopropanol, ethylene glycol, diethylene glycol, propylene glycol, and glycerol; ester solvents such as ethyl acetate and butyl acetate; and 2-pyrrolidone; N-methyl-2-pyrrolidone. These solvents can be suitably selected based on the application or the like of the fluorescent ink composition, and employed singly or as mixtures of two or more solvents.

The above resin (binder) is desirably one that can fix the coordination polymer well to the substrate and will dissolve well in the above solvent. The resin can be optically transparent or opaque. Examples are polyvinyl resins, phenol resins, amino resins, polyamide resins, nylon resins, polyolefin resins, acrylic resins, epoxy resins, urethane resins, cellulose resins, polyester resins, silicone resins, and fluorine-based resins. These resins can be suitably selected based on the application or the like of the fluorescent ink composition, and can be employed singly or in combinations of two or more.

The penetrating agent is added with the goal of accelerating penetration of the ink composition into paper or the like and accelerating the apparent drying property. Examples of penetrating agents are glycol ether, alkylene glycol, sodium lauryl sulfate, sodium oleate, sodium dodecylbenzene sulfonate, and sodium dioctyl sulfosuccinate. These penetrating agents can be employed singly or in combinations of two or more.

The defoaming agent is added with the goal of preventing the generation of bubbles during movement and during manufacturing of the ink composition. An anionic, nonionic, cationic, or amphoteric surfactant can be employed as the defoaming agent. Examples of anionic surfactants are fatty acid salts, alkyl sulfates, alkyl phosphates, and alkyl ether phosphates. Examples of nonionic surfactants are polyoxyethylene alkyl ethers, polyoxyethylene alkylaryl ethers, polyoxyethylene oxypropylene block copolymers, sorbitan fatty acid esters, glycerol fatty acid esters, polyoxyethylene fatty acid esters, polyoxyethylene alkyl amines, and fluorine-based and silicone-based compounds. Examples of cationic surfactants are quaternary ammonium salts and alkyl pyridinium salts. Examples of amphoteric surfactants are alkyl betaine, alkyl amine oxides, and phosphatidyl choline. These surfactants can be employed singly or in combinations of two or more.

Examples of the above dispersing agent are surfactants such as stearic acid soap, oleic acid soap, rosin acid soap, Na-di-β-naphthylmethane disulfate, sodium lauryl sulfate, sodium diethylhexyl sulfosuccinate, and sodium dioctyl sulfosuccinate. These surfactants can be employed singly or in combinations of two or more.

A known pigment or dye can be employed as the colorant. Examples are organic dyes and pigments such as azos, azomethines, quinacridones, anthraquinones, dioxazines, quinolines, perylenes, isoindolinones, and quinoophthalones. These colorants can be employed singly or in combinations of two or more.

The content of the various above additives in the fluorescent ink composition of the present invention is not specifically limited and can be suitably set based on the type of substrate, application, and the like. The content of the resin (binder) in the fluorescent ink composition of the present invention is desirably 0.5 to 30 mass %, preferably 1 to 10 mass %. When the content of the resin is less than 0.5 mass %, the coordination polymer cannot be suitably fixed to an impermeable substrate. When the content of the resin exceeds 30 mass %, the area around the coordination polymer in the fluorescent ink composition is thickly covered by resin (binder), running the risk of decreased light emission by the coordination polymer.

<Coordination Polymer-Containing Plastic>

The present invention covers a luminescent plastic composition containing the coordination polymer of the present invention. The plastic material that is employed in the luminescent plastic composition is not specifically limited. Various materials can be utilized. Examples of plastic materials are polyethylene resins, polypropylene resins, polyvinyl chloride resins, urea resins, fluororesins, polyester resins, polyamide resins, polyacetal resins, polycarbonate resins, polyarylate resins, polysulfone resins, polyphenylene sulfide resins, polyether sulfone resins, polyallylsulfone resins, polytetrafluoroethylene resins, phenol resins, unsaturated polyester resins, epoxy resins, polyimide resins, and polyamide-imide resins. The method of blending the coordination polymer and molding is not specifically limited. Examples are injection molding, blow molding, compression molding, extrusion molding, reaction molding, hollow molding, heat molding, and FRP molding.

EXAMPLES

The present invention is further described in detail based on Examples. However, Examples are exemplifications of the present invention and do not intend to limit the present invention.

Reference Example 1-1. Preparation of Eu(hfa)$_3$(H$_2$O)$_2$

Europium acetate tetrahydrate (5.0 g, 13.6 mmol) was dissolved in distilled water (20 mL). To the aqueous solution was added dropwise a solution of hexafluoroacetylacetone (7.0 g, 33.6 mmol). The obtained reaction solution was stirred for 3 hours at room temperature, resulting in production of a yellowish white precipitate. The reaction solution was filtered to recover the precipitate. The obtained precipitate was used in the next step without further purification.

Yield: 95%; IR (KBr): 1650, 1258-1145 cm$^{-1}$; Elemental analysis calcd (%) for C$_{15}$H$_7$EuF$_{18}$O$_8$: C, 22.27; H, 0.87. found: C, 22.12; H, 1.01.[1]

(1). Y. Hasegawa, T. Ohkubo, T. Nakanishi, A. Kobayashi, M. Kato, T. Seki, H. Ito and K. Fushimi: *Eur. J. Inorg. Chem.* 2013 (2013) 5911.

Reference Example 1-2. Preparation of Tb(hfa)$_3$(H$_2$O)$_2$

Terbium acetate tetrahydrate (5.0 g, 12.3 mmol) was dissolved in distilled water (20 mL). To the aqueous solution was added dropwise a solution of hexafluoroacetylacetone (7.0 g, 33.6 mmol). The obtained reaction solution was stirred for 3 hours at room temperature, resulting in production of a yellowish white precipitate. The reaction solution was filtered to recover the precipitate. The obtained precipitate was used in the next step without further purification.

Yield: 70%; IR(KBr): 1650, 1255-1141 cm$^{-1}$; Elemental analysis calcd (%) for [C$_{15}$H$_7$F$_{18}$O$_8$Tb+H$_2$O]: C, 21.60; H, 1.09. found: C, 21.47; H, 1.34.[2]

(2). S. Katagiri, Y. Tsukahara, Y. Hasegawa, and Y. Wada: *Bull. Chem. Soc. Jpn.* 80 (2007) 1492.

Example 1. Synthesis of a Complex from a Mono-Carboxy Ligand (1) Ligand [4-carboxyphenyl] diphenyl Phosphine Oxide (Hereinafter CPO)
[C12]

Scheme 1: Synthesis of CPO

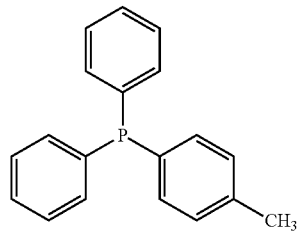

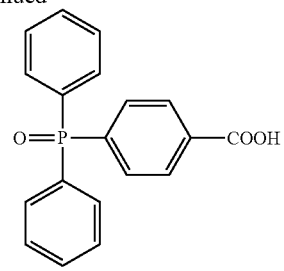

-continued

The synthesis was performed at a tenth scale of the published data (C. M. Friesen et al, *Journal of Fluorine Chemistry* 2012, 144, 24-32). In a 50-mL pear-shaped evaporating flask, diphenyl[(4-methyl)phenyl]phosphine (1.01 g, 3.2 mmol) and NaOH (0.22 g, 5.6 mmol) were placed which were dispersed in distilled water (30 mL). To the dispersion was added KMnO$_4$ (2.22 g, 14 mmol) in four portions and refluxed under heating at 100° C. for 12 hours. After 12 hours, it was observed that the colour of the precipitate changed to brown and then the precipitate was filtered through a filter paper and washed with warm water. To the obtained filtered liquid was added 10 M H$_2$SO$_4$, resulting in generation of a white precipitate. The precipitate was dissolved in 10% NaOH and the aqueous solution was extracted with Et$_2$O. To the obtained aqueous layer was again added 10 M H$_2$SO$_4$ and the generated white precipitate was collected through a filter paper. The obtained precipitate on the filter paper was dried under vacuum at 75° C. After 4 hours, a white solid in the shape of paper was obtained.

Yield: 0.555 g (54%). $^1$H NMR (400 MHz, DMSO, TMS): δ8.10-8.06 (dd, 2H), δ7.78-7.72 (dd, 2H), δ7.67-7.61 (m, 6H), δ7.60-7.54 (td, 4H).

IR(ATR): 1701, 1434, 1250, 1154, 1122, 1104, 1086, 933 cm$^{-1}$.

(2) Synthesis of Complex 1

In a 50-mL pear-shaped evaporating flask, the ligand CPO (207 mg, 0.64 mmol) and Eu(hfa)$_3$(H$_2$O)$_2$ (720 mg, 0.89 mmol) were placed and dispersed in 30 mL MeOH. The dispersion was refluxed under heating at 60° C. for 5 hours. The obtained precipitate was washed with MeOH and subjected to suction filtration. The obtained substance was dried under vacuum to give white powder.

Yield: 45.3 mg. IR(ATR): 1658, 1592, 1540, 1498, 1411, 1254, 1144, 1118 cm$^{-1}$.

Example 2. Synthesis of a Complex from a Tri-Carboxy Ligand (1) Ligand [4,4',4"-tricarboxyphenyl] phosphine Oxide (Hereinafter TCPO)
[C13]

Scheme 2: Synthesis of TCPO

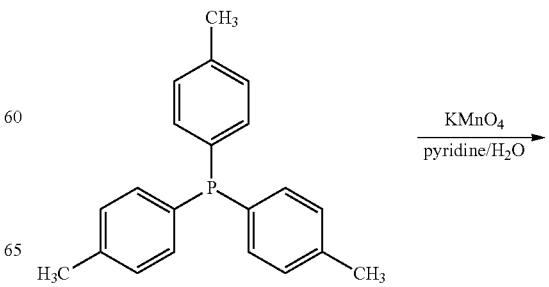

-continued

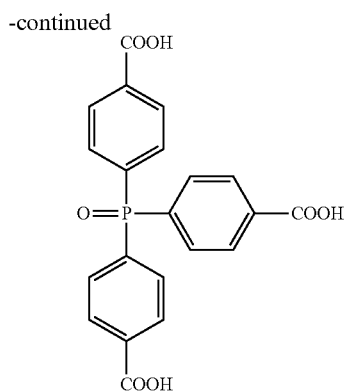

The synthesis was performed at a half scale of the published data (J. Vaclavik, M Servalli et al, *Chem Cat Chem* 2013, 5, 692-696). In a 100-mL pear-shaped evaporating flask, tri(p-toryl)phosphine (1 g, 3.2 mmol) was dispersed in pyridine (12 mL)/distilled water (24 mL). While heating the dispersion, $KMnO_4$ (10 g, 63.3 mmol) was added in four portions and refluxed under heating at 100° C. for 48 hours. After 48 hours, the reaction solution was filtered through a filter paper and the precipitate was washed with warm water. When 10 M $H_2SO_4$ was added to the obtained filtered liquid, a white precipitate was obtained. The precipitate was dissolved in 2 M NaOH and the aqueous solution was extracted with THF and EtOAc. To the obtained aqueous layer was again added 10 M $H_2SO_4$ and the generated white precipitate was recovered by suction filtration. The obtained precipitate was dried under vacuum to give white powder.

Yield: 0.433 g (34%). $^1$H NMR (400 MHz, DMSO, TMS): δ8.12-8.08 (dd, 6H), δ7.88-7.75 (dd, 6H).

IR(ATR): 1692, 1395, 1246, 1162, 1102, 1016, 857 cm$^{-1}$.

(2) Synthesis of Complex 2

In a 50 mL pear-shaped evaporating flask, the ligand TCPO (260 mg, 0.63 mmol) and $Eu(hfa)_3(H_2O)_2$ (720 mg, 0.89 mmol) were placed and dispersed in 30 mL MeOH. The dispersion was refluxed under heating at 60° C. for 9 hours. The obtained precipitate was washed with MeOH and subjected to suction filtration. The obtained substance was dried under vacuum to give white powder.

Yield: 294.7 mg

IR(ATR): 1624, 1548, 1398, 1382, 1185, 1145, 1116, 1050, 1018, 866 cm$^{-1}$.

Example 3. Property Measurements (1) XRD Measurement

XRD measurement was conducted on RIGAKU RINT 2000 Ultima over a measurement range of 10° to 40° at a scan speed of 0.500 rad/min.

(2) SEM Measurement

SEM measurement was conducted on JEOL JSM-6500F.

(3) Thermogravimetry (TG) Measurement

Complex 1 and complex 2 as samples and $Al_2O_3$ as a reference were used (7 mg each). The analytical device used was EXSTAR 6000 (TG DTA 6300). Complex 1 was measured during only one heating process over a measurement range of 30° C. to 500° C. at a heating rate of 1° C./min. As complex 2 showed a big weight loss at or below 100° C., complex 2 was once heated to 100° C. at a heating rate of 1° C./min and cooled and then the measurement was conducted over a measurement range of 50° C. to 500° C. at a heating rate of 1° C./min.

(4) Emission Spectrometry

Each complex (powder) was analysed. Measurement was conducted on Fluorolog-3 Spectrofluorometer with a quartz cell for powder over a measurement range of 550-720 nm at a scan speed of 0.05 nm/min and an excitation wavelength of 365 nm.

(5) Emission Lifetime Measurement

Each complex (powder) was analysed. Measurement was conducted on Fluorolog-3 Spectrofluorometer with a quartz cell for powder at a detection wavelength of 610 nm.

(6) Measurement and Calculation of Emission Quantum Yield

Each complex (powder) was analysed. Measurement was conducted on JASCO FP-6600 with a quartz cell for powder over a measurement range of 300-700 nm when an excitation wavelength was 365 nm and a measurement range of 400-700 nm when an excitation wavelength was 465 nm at a scanning speed of 20 nm/min.

The calculation was carried out with Igor. With the respective measurement results, differential spectra (background measurement−sample measurement) were generated and spectra on the side of excitation light and the side of detection were respectively integrated. The emission quantum yield was determined with the following equation 1.

$$\text{Emission quantum yield } \Phi \text{ [\%]} = (\text{emitted area})/(\text{absorbed area}) \times 100 \quad (1)$$

The energy conversion efficiency was determined with the following equation 2.

[M 1]

$$\eta = \Phi_{\pi\pi^*}/\Phi_{4f4f} \quad (2)$$

(7) Titration Absorbance Measurement

In order to determine the proportion of ligands required for complex 1, absorbance was measured every time after dripping a certain amount of ligand, thereby generating a titration curve. With MeOH as a solvent, a $4.0 \times 10^{-5}$ M $Eu(hfa)_3(H_2O)_2$ solution (solution I) and a $6.0 \times 10^{-4}$ M CPO solution (solution II) were prepared. Solution I (3 mL) was placed in a cell for spectrometry and regarded as a ligand of 0 equivalent. To the cell was added a 20-μL portion, i.e., 0.1 equivalent, of Solution II and measurement was carried out up to 2.0 equivalent of ligand in total. Measurement was conducted on JASCO V-550 (UV/VIS Spectrophotometer) with a 1 cm×1 cm quartz cell with four planes in a measurement range of 200-500 nm at a scanning speed of 100 nm/min.

(8) Thermoluminescence Measurement

In order to examine heat resistance related to luminescence, luminescence was measured while heating.

Each of complex 1, complex 2 and $Eu(hfa)_3(TPPO)_2$, as a mononuclear complex for comparison, was mounted on a glass slide which was covered with another glass slide and observed for luminescence under heating on a hot plate (FIG. 1). Complex 2 was observed while recording emission spectrum at every certain temperature increase. The observation was conducted on OceanOptics USB4000.

Measurement Results (1) Structure of Complexes

Figure 2:
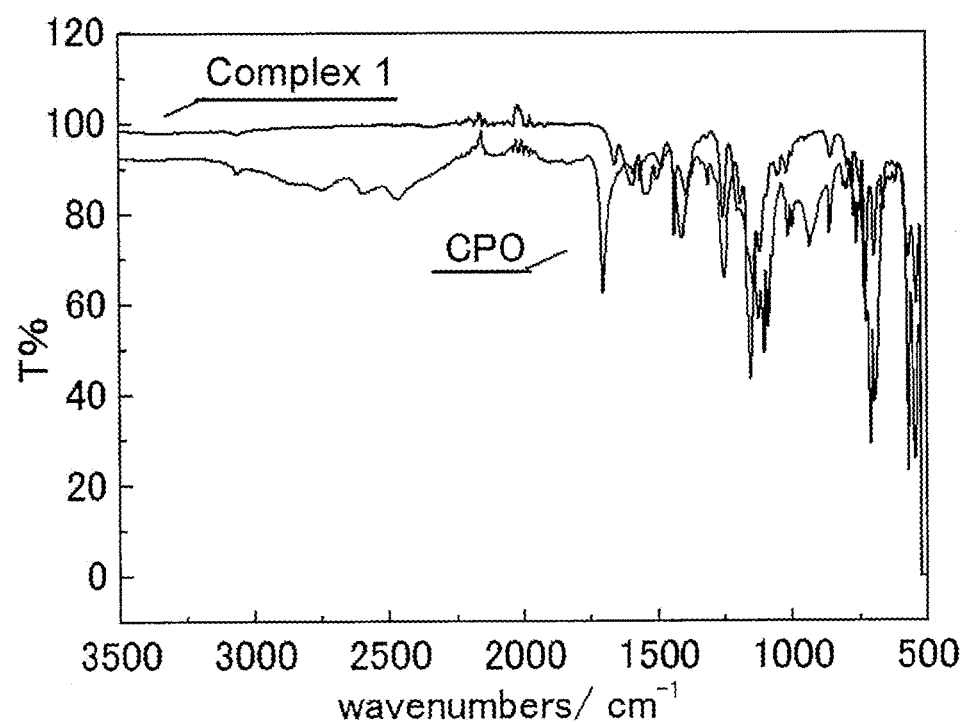
FIG. 2 shows the result of IR measurement comparing a ligand CPO and complex 1.
Figure 3:
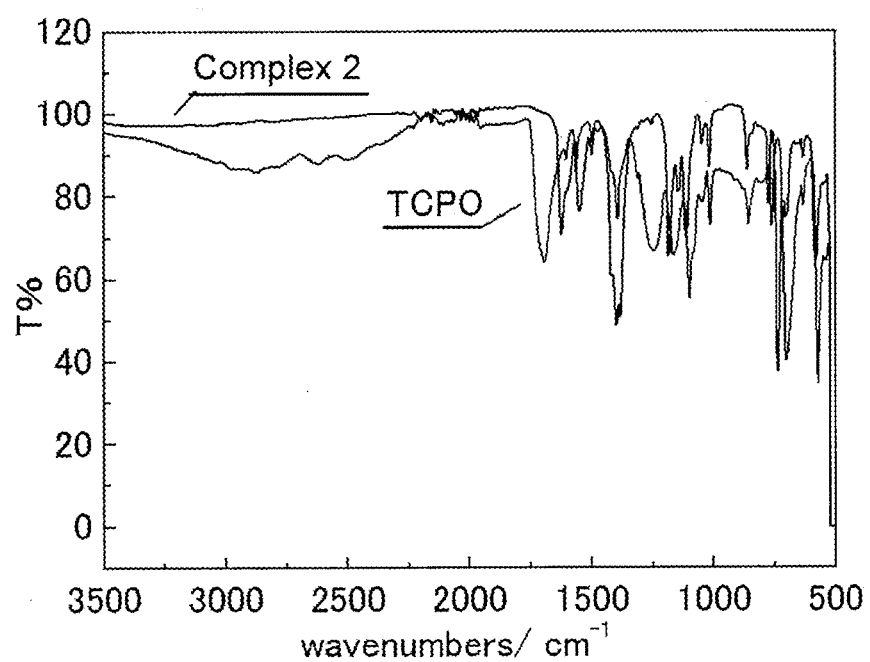
FIG. 3 shows the result of IR measurement comparing a ligand TCPO and complex 2.

Because starting material ligands CPO and TCPO were not completely soluble in MeOH, each complex was synthesized while the ligands were dispersed. The obtained complexes were both insoluble in MeOH and water. Because of this, it was estimated that the complexes were in the form of coordination polymers with both the phosphine oxide moiety and the carboxyl group serving as coordination sites. Because it was not possible to use structural analysis methods such as single crystal X-ray structural analysis, the structures were estimated by IR and FAB-MS. The results of IR measurement comparing each ligand and complex are shown in FIGS. 2 and 3.

The broad absorbance in the range of 2500 to 3000 $cm^{-1}$ which could be observed in the IR measurement results of ligands disappeared in both complexes. As the absorbance resulted from the —OH group in carboxylic acid, it is suggested that the —OH group is disappeared by formation of complexes. Based on this idea, it is expected that carboxylic acid does not remain in the form of —COOH in complex 2 either. Because the absorbance around 1700 $cm^{-1}$ resulting from the —C=O moiety in carboxylic acid shifted towards the low frequency side, it is estimated that another substance coordinates with carboxylic acid to suppress oscillation. These results indicate that not only the phosphine oxide moiety but also a carboxyl group serves as coordination sites.

Partial structures of complex 1 and complex 2 predicted from the above results are shown below.

Predicted Partial Structure of Complex 2

From the result of FAB-MS on complex 1, m/z=1569 of the enclosed structure (Eu(IIL)×2+ligand×2+hfa×3) in the above chemical structural formula was detected. From this result, it is confirmed that both the phosphine oxide moiety and the carboxyl group serve as coordination sites for Eu(III).

As complex 2 contains three carboxyl groups in a ligand, there are many predictable structural patterns and thus no structure has been drawn that completely conforms to the FAB-MS result. As many peaks at m/z=2000 to 3500 which are not from matrix are observed, it is suggested that complex 2 is also a coordination polymer.

(2) Evaluation of Properties 2.1. SEM Measurement

Figure 4A:
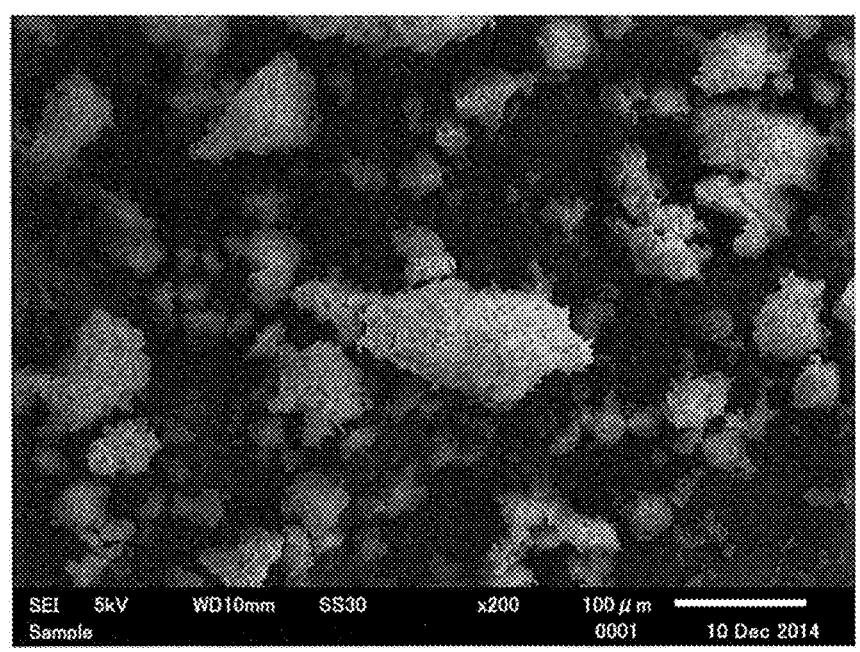
FIG. 4A shows a SEM image (×200) of complex 1.
Figure 4B:
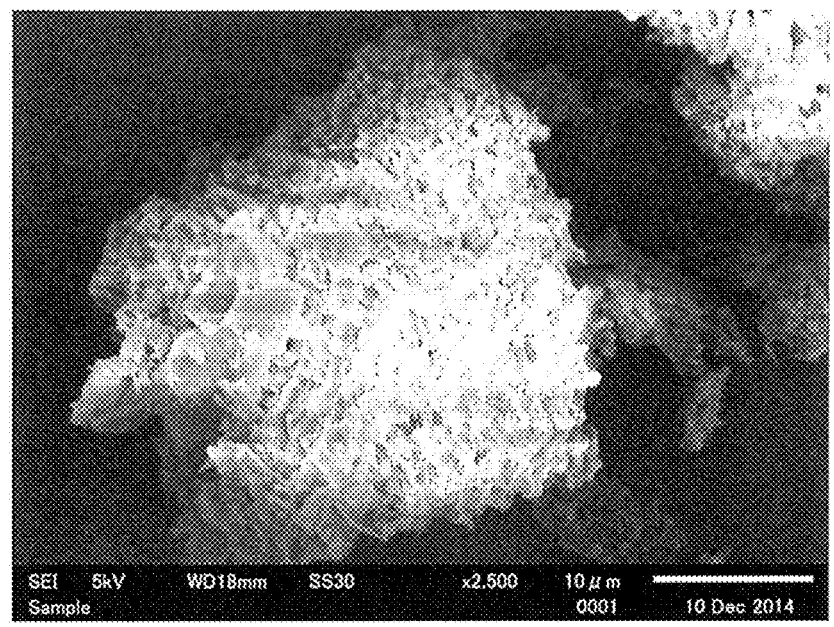
FIG. 4B shows a SEM image (×2500) of complex 1.
Figure 4C:
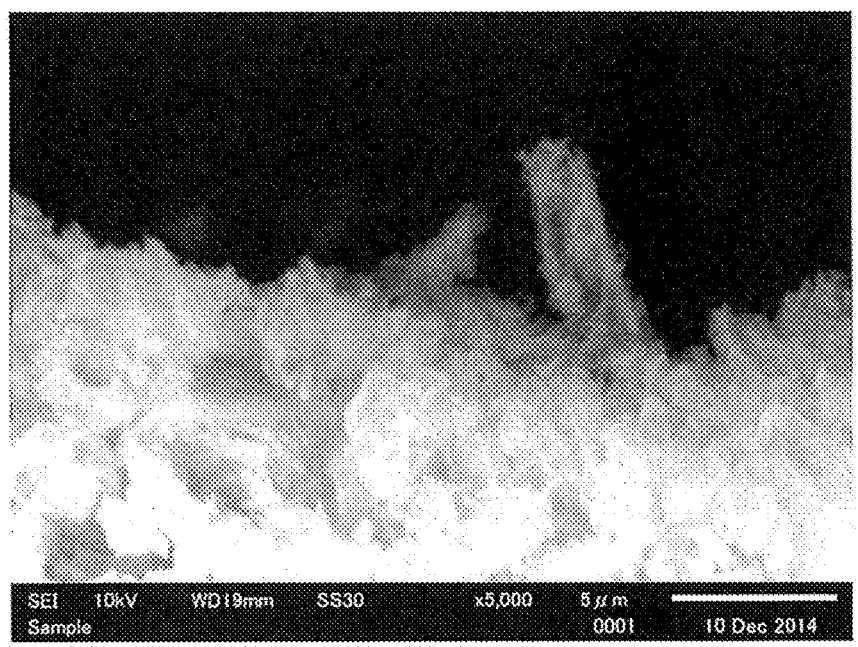
FIG. 4C shows a SEM image (×5000) of complex 1.

The images obtained by SEM measurement of complex 1 are shown in FIGS. 4A to 4C.

The shape of paper-like pieces of scales can be observed. Under a higher magnification, a fluffy structure is observed. While handling complex 1, complex 1 tended to be electro-

[C14]

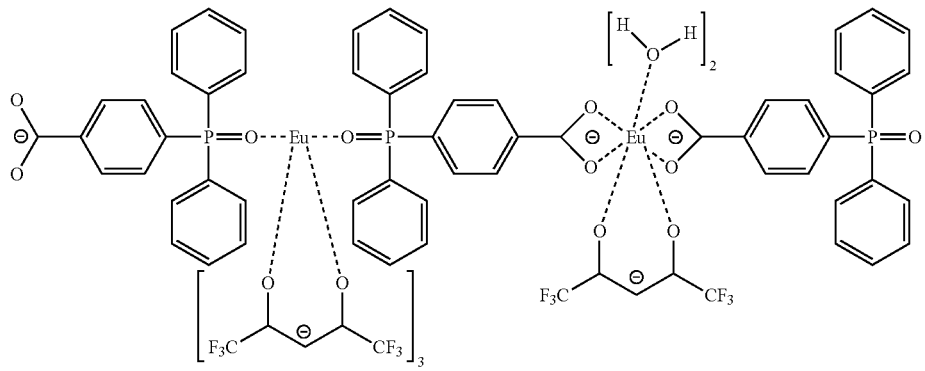

Predicted Partial Structure of Complex 1

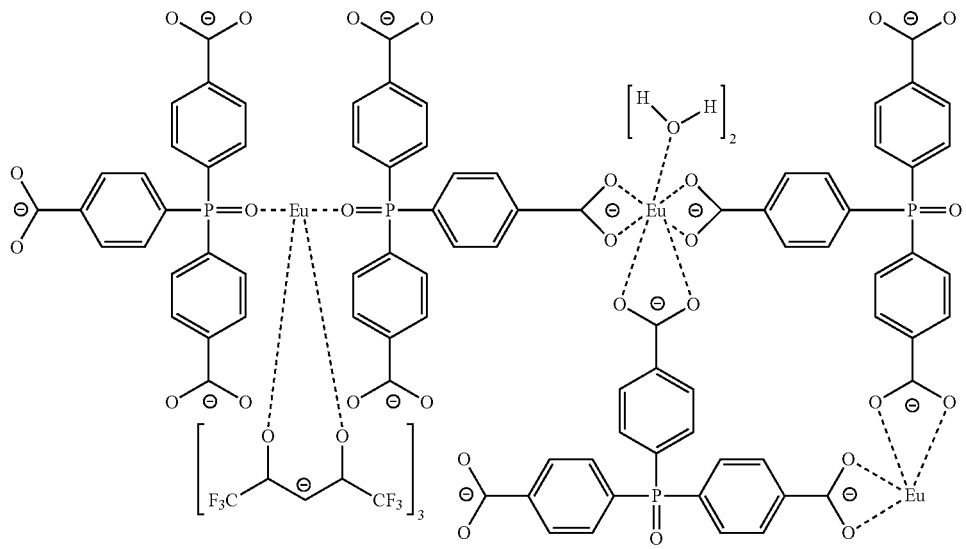

statically charged. The structure like a tissue paper, as can be seen from the SEM images, may be one of the reasons therefor.

2.2. XRD measurement

Figure 5:
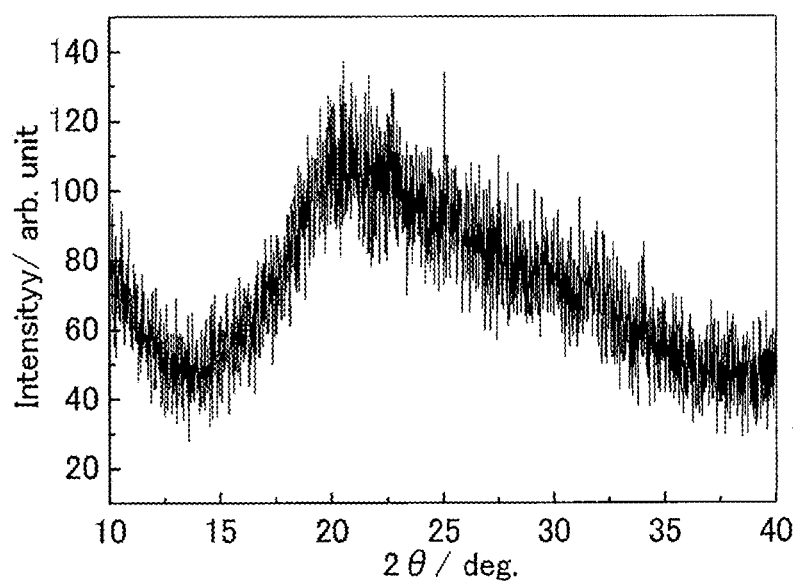
FIG. 5 shows the result of XRD measurement of complex 1.
Figure 6:
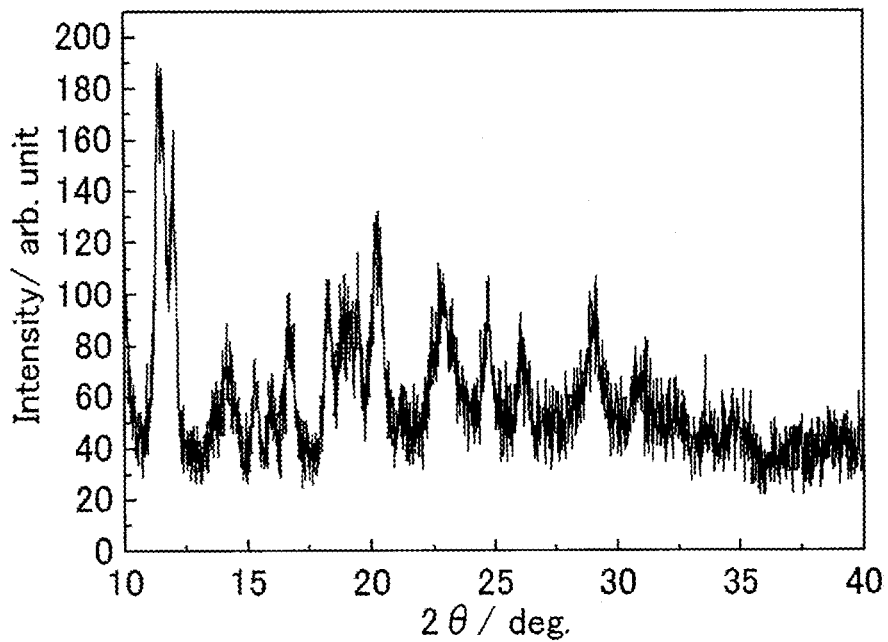
FIG. 6 shows the result of XRD measurement of complex 2 (before heating).
Figure 7:
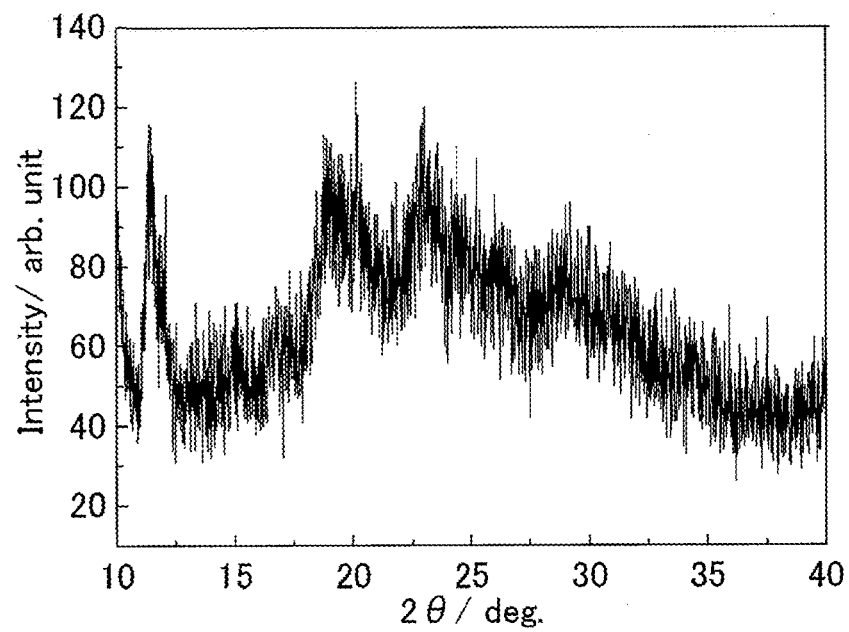
FIG. 7 shows the result of XRD measurement of complex 2 (after heating).

The results of XRD measurements of complexes 1 and 2 are shown in FIGS. 5 to 7.

For complex 1 shown in FIG. 5, no notable peak was observed and thus it was estimated that complex 1 had low crystallinity.

For complex 2 (before heating) shown in FIG. 6, relatively strong peaks were detected in XRD measurement on the complex immediately after synthesis without application of heat, and thus good crystallinity is suggested. However, when a sample (FIG. 7) after drying in a vacuum oven at 90° C. for 2 hours was measured under the same conditions, many peaks disappeared. This means that drying in a vacuum oven at 90° C. for 2 hours caused elimination of coordinated water, resulting in the crystal structure change.

2.3. Thermogravimetry (TG) Measurement

Figure 8:
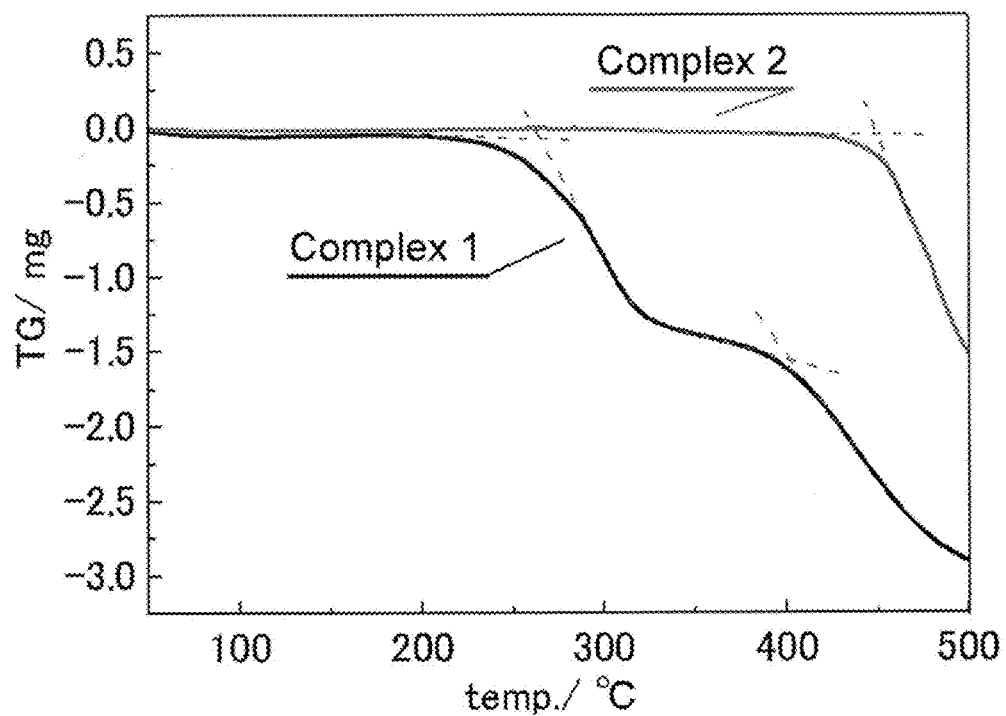
FIG. 8 shows the result of TG measurement of complexes 1 and 2.
Figure 9:
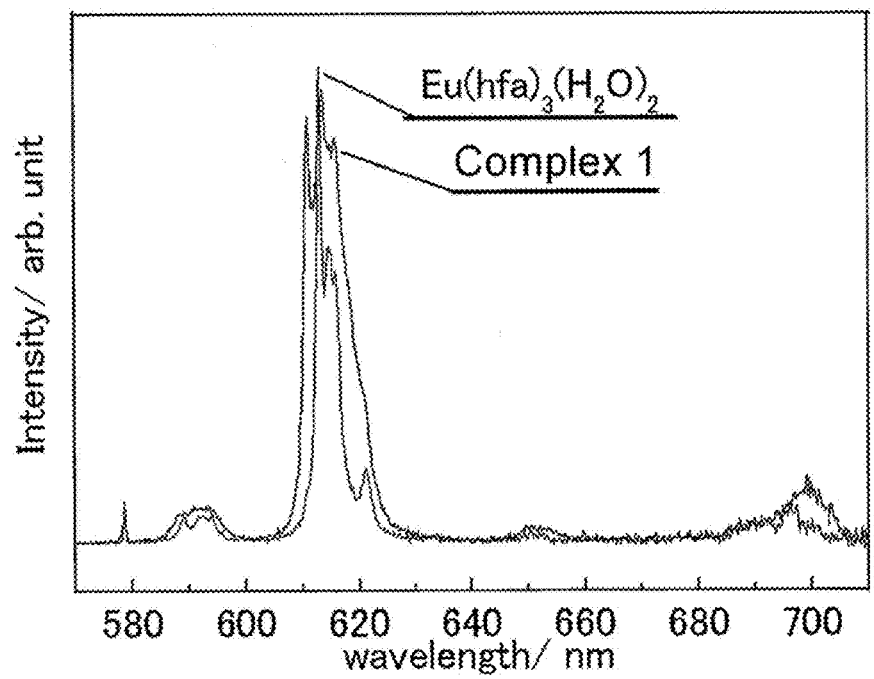
FIG. 9 shows an emission spectrum of complex 1.
Figure 10:
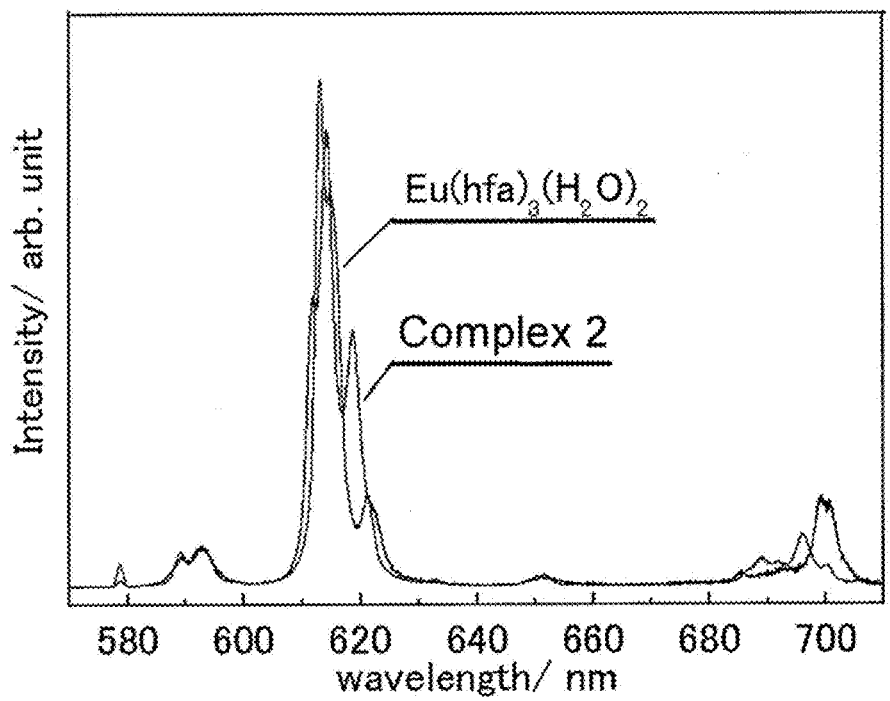
FIG. 10 shows an emission spectrum of complex 2 (before heating).
Figure 11:
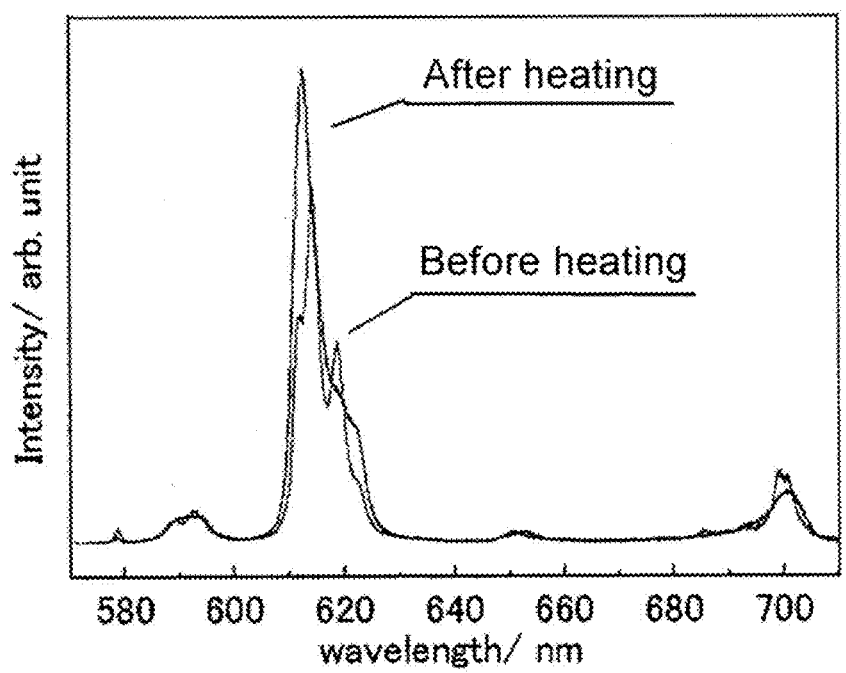
FIG. 11 shows comparison of emission spectra between complex 2 (before and after heating).

The results of TG measurements of complex 1 and complex 2 are shown in FIG. 8.

For complex 2, only the result of the measurement during the second heating process over a measurement range of 50° C. to 500° C. is shown. For comparison, the result for complex 1 shown in also only over the range of 50° C. to 500° C. This figure is drawn with regarding the weight at 50° C. as 0 μg.

From the figure, decomposition points at 264° C. and 399° C. are observed for complex 1, indicating that complex 1 is decomposed in two phases. A decomposition point at 450° C. only was observed for complex 2, revealing high thermostability. The weight losses of the complexes at 500° C. from 0° C. were 46% and 37% for complex 1 and complex 2, respectively. This result also shows that complex 2 has high thermostability.

The weight losses at or below 100° C. were 2% and 10% for complex 1 and complex 2, respectively. From this result, it is suggested that complex 2 has a structure that is liable to contain organic solvent or water.

(3) Evaluation of Photophysical Properties 3.1. Emission Spectrum Measurement

The emission spectra of the complexes are shown below. The intensity of each spectrum was normalised by $^5D_0 \rightarrow {}^7F_1$ magnetic dipole transition.

Both complexes are different in the shape of the spectrum from $Eu(hfa)_3(H_2O)_2$, and thus it can be said that novel Eu complexes were successfully synthesised. When focusing on the spectra based on $^5D_0 \rightarrow {}^7F_2$ electric dipole transition, the spectrum of complex 1 is significantly broader than that of $Eu(hfa)_3(H_2O)_2$. It is believed that, although it is more specifically described in the section of emission lifetime measurement hereinbelow, this is due to the presence of two emission sites. With regard to the spectrum based on $^5D_0 \rightarrow {}^7F_4$ electric dipole transition, the intensity was about 2 times higher and the spectrum shifted to the long-wavelength side.

As complex 2 shows a significant change in the spectrum before and after heating with the peak top position being shifted, it is apparent that, in conjunction with the result of XRD measurement, the structure is changed. It is believed that heating caused elimination of coordinated water in the complex, resulting in the structure change. Accordingly, the reason that the normalisation intensity is higher after heating is believed to be due to elimination of coordinated water resulting in a reduction in vibrational deactivation of coordinated water.

3.2. Emission Lifetime Measurement

Figure 12:
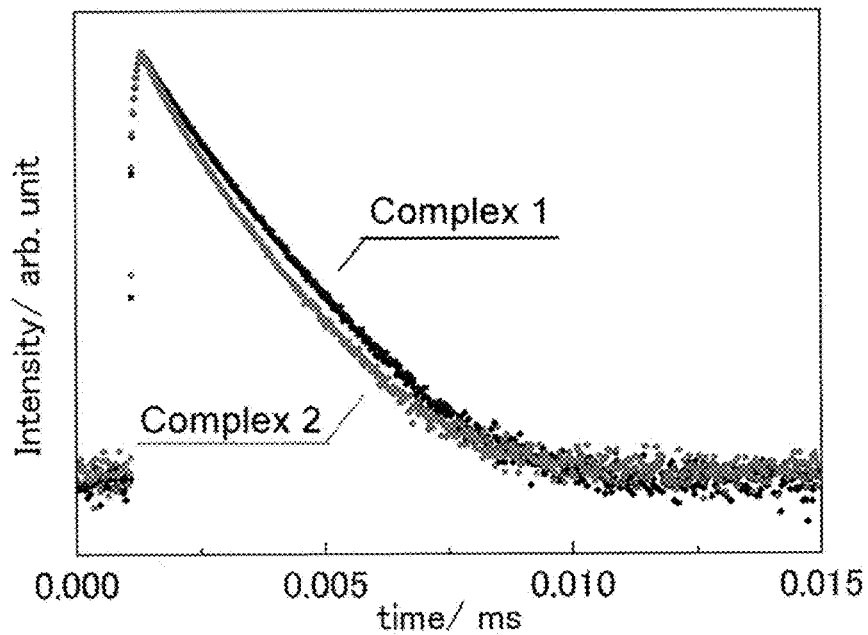
FIG. 12 shows the result of emission lifetime measurement of complexes 1 and 2 (before heating).
Figure 13:
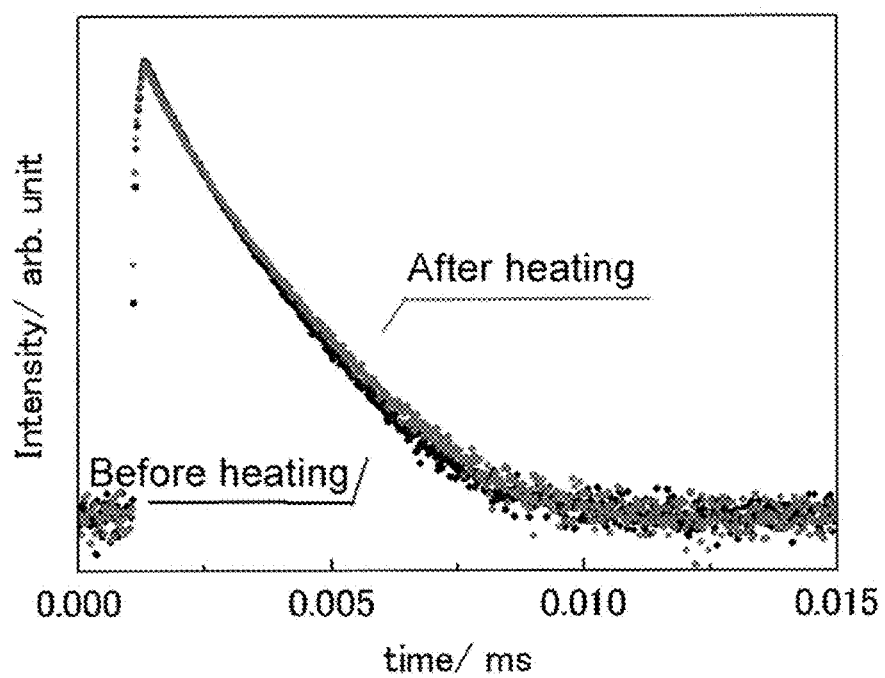
FIG. 13 shows the result of emission lifetime measurement of complex 2 (before and after heating).

FIGS. 12 and 13 show plots of the obtained data on single logarithmic charts.

The obtained data were analysed on OriginPro 7. When the data were sought to be fitted to a function, both complexes showed good fitting to the binary system. The fitting used and the calculated emission lifetime are shown below.

[Math. 2]

Function name: ExpDecay2

$$y = y_0 + A_1 e^{-(x-x_0)/t_1} + A_2 e^{-(x-x_0)/t_2} \quad (3)$$

TABLE 1

| Emission lifetime of complexes | | |
|---|---|---|
| | τ1 (proportion) | τ2 (proportion) |
| Complex 1 | 0.48 ms (67%) | 0.97 ms (33%) |
| Complex 2 (before heating) | 0.42 ms (84%) | 0.90 ms (16%) |
| Complex 3 (after heating) | 0.35 ms (63%) | 0.76 ms (37%) |

When complex 1 and complex 2 before heating are compared, complex 2 has a 10% or more increase in the proportion of $\tau_1$, and thus it is expected that the lifetime component of complex 2 is derived from carboxyl groups. However, after heating, complex 2 has a decreased proportion of $\tau_1$ and a decreased length of $\tau_2$ which is a long lifetime component. From the result, it is expected that the coordination geometry is significantly changed.

3.3. Emission Quantum Yield

The values calculated from the obtained data are summarised in Table 3.

TABLE 2

| Emission quantum yield of complexes | | | |
|---|---|---|---|
| | $\Phi_{\pi\pi*}$ | $\Phi_{4f4f}$ | η |
| Complex 1 | 22% | — | — |
| Complex 2 (before heating) | 25% | 28% | 0.89 |
| Complex 2 (after heating) | 20% | 26% | 0.79 |

The column of $\Phi_{4f4f}$ [M 3]

for complex 1 is left blank because of the impractical value possibly because of an extremely low amount of the sample leading to insufficient exposure to excitation light.

The results in the section of emission spectrum described above are now reviewed. From the comparison of spectra normalised with the emission intensity by $^5D_0 \rightarrow 7F$, magnetic dipole transition, the emission intensity by $^5D_0 \rightarrow {}^7F_2$ electric dipole transition was increased after heating compared to before heating. The emission intensity by $^5D_0 \rightarrow {}^7F_4$ electric dipole transition was decreased after heating; however, when the emission intensities are compared in terms of the area, it can be regarded that the emission intensity is increased after heating.

3.4. Titration Absorbance Measurement

Figure 14:
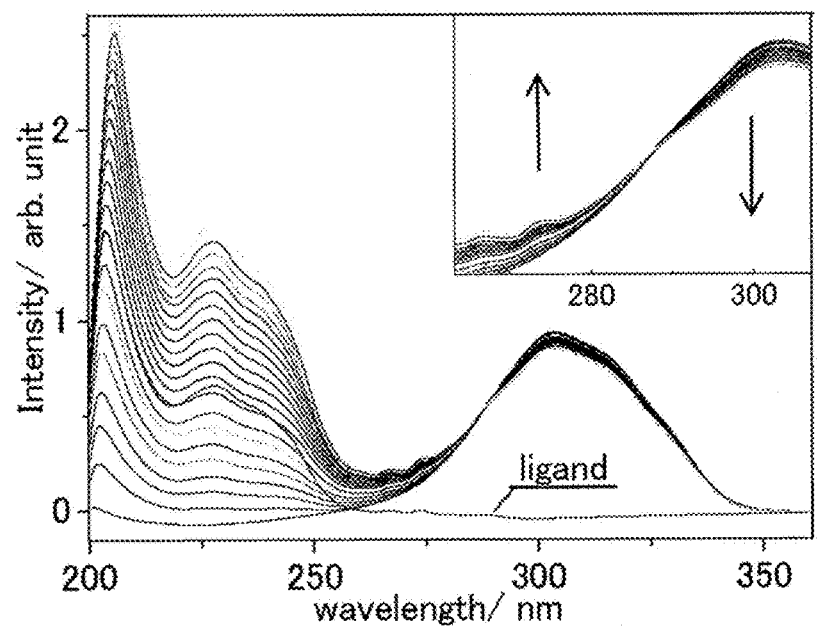
FIG. 14 shows the result of titration absorbance measurement (the inset is a magnified view).

The result of the titration absorbance measurement experiment is shown in FIG. 14. Absorbance spectra of $Eu(hfa)_3(H_2O)_2$ solutions in which the ligand contained therein is increased from 0 equivalent to 2.0 equivalent at 0.1 equivalent intervals and absorbance spectrum of a solution containing only the ligand CPO are also shown in the same figure, with the magnified view being shown in the inset. The spectra for which the absorbance intensity is the lowest and the highest at the wavelength of 200 nm correspond to the spectra of the solution in which the amount of the ligand is 0 equivalent and the solution in which the amount of the ligand is 2.0 equivalent, respectively.

Figure 15:
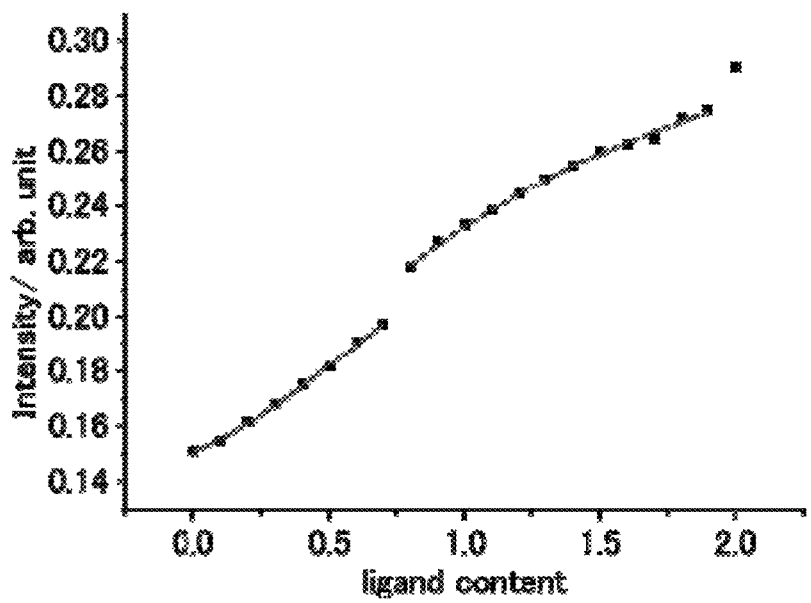
FIG. 15 shows the change in the absorbance intensity at an increment peak 273.8 nm.
Figure 16:
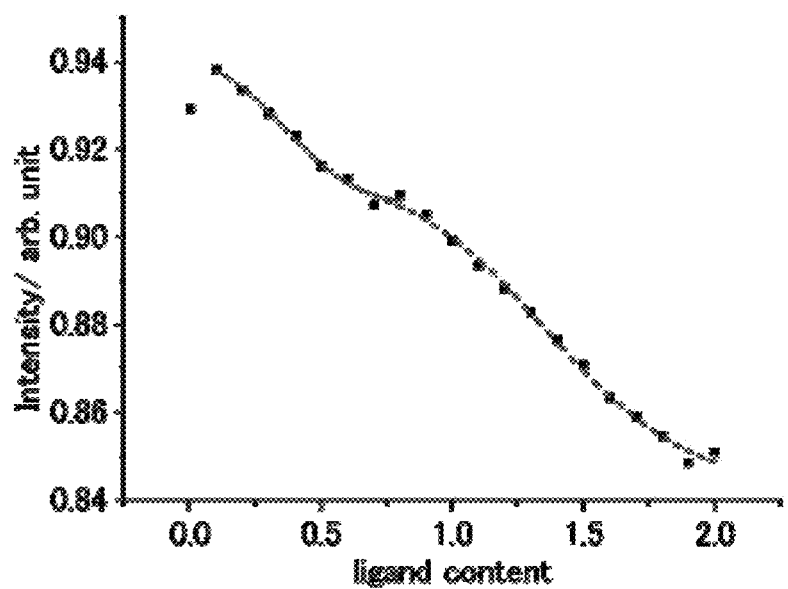
FIG. 16 shows the change in the absorbance intensity at a decrement peak 303.0 nm.

The tendency observed is that the absorbance intensity increased with an increase in the amount of the ligand at a wavelength lower than 288 nm, while, conversely, the absorbance intensity decreased with an increase in the amount of the ligand at a wavelength higher than 288 nm. In the region at or lower than 288 nm, the projecting shape resulting from the shape of the absorbance peak of the ligand is more notable. In order to facilitate visualisation of the change in the absorbance intensity, the magnitude of the absorbance intensity relative to the amount of the ligand at 273.8 nm, which is a peak of increment, and 303.0 nm, which is a peak of a decrement, was plotted, results of which are shown in FIGS. 15 and 16, respectively.

The plots are distributed on each of two lines having similar gradient. Between 0.7 equivalent and 0.8 equivalent, a distinct plot behaviour from the neighbourhood was exhibited. It is possible that some chemical reaction occurred in this region. Also in the region of 1.9 to 2.0 equivalent, one plot is displaced which may exhibit a similar change. Because of these, the complex formation may be a reaction including more than one process.

3.5. Thermoluminscence Measurement

Figure 17:
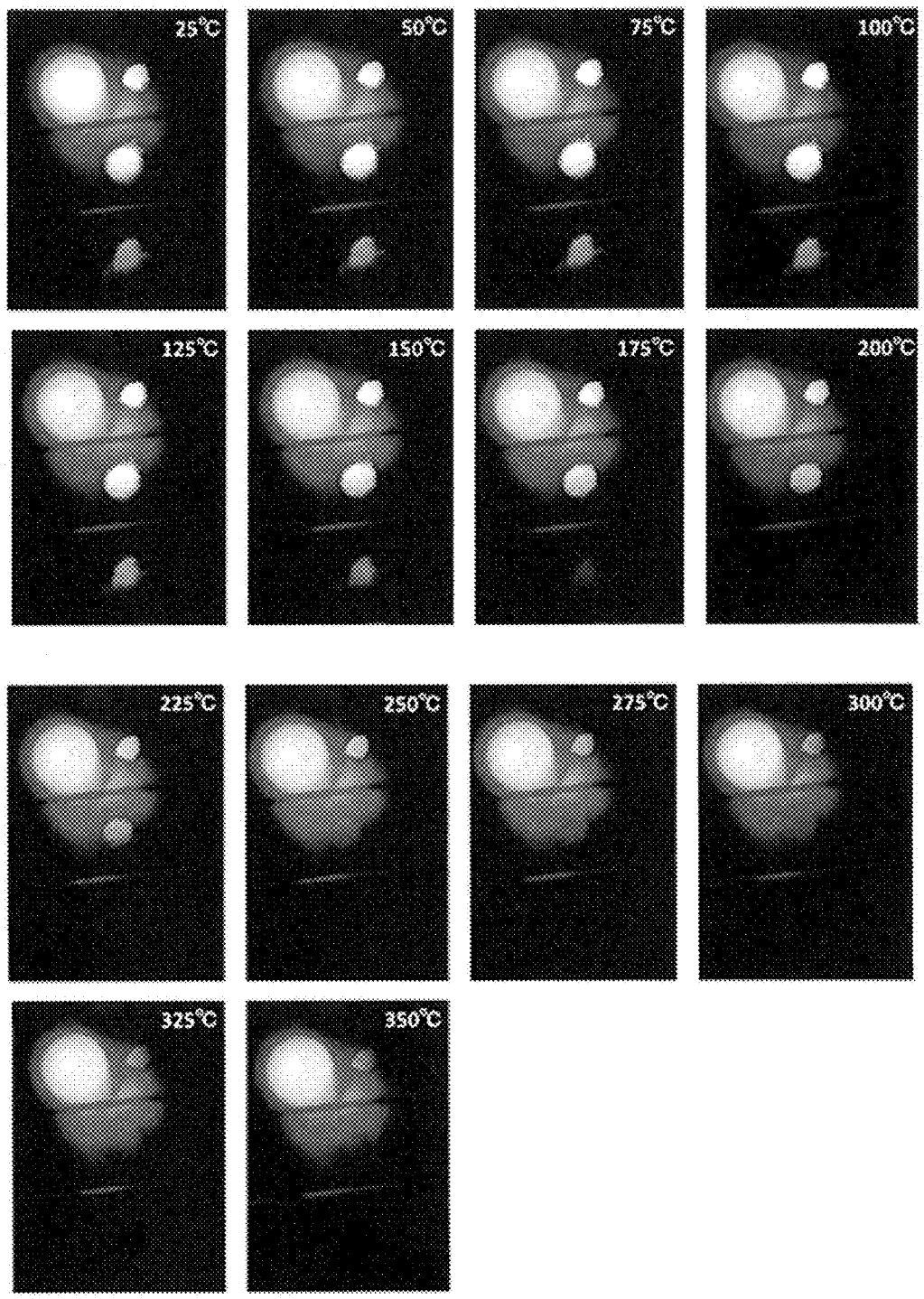
FIG. 17 shows thermoluminescence (upon heating); top: complex 1, middle: complex 2, bottom: $Eu(hfa)_3(TPPO)_2$.
Figure 18:
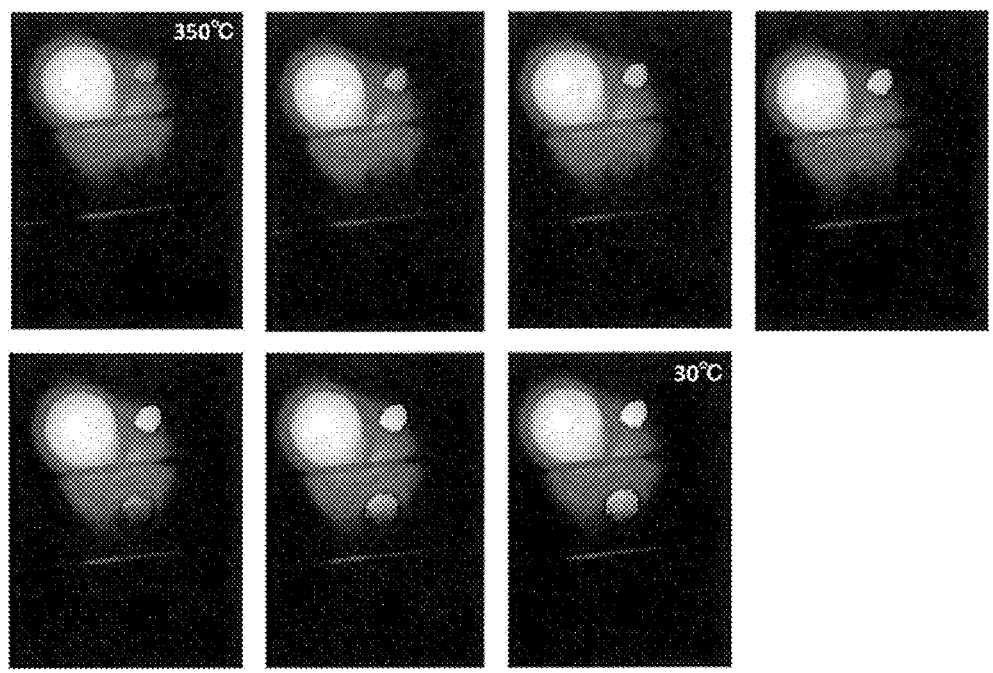
FIG. 18 shows thermoluminescence (upon cooling); top: complex 1, middle: complex 2, bottom: $Eu(hfa)_3(TPPO)_2$.

Luminescence during heating and cooling at the respective temperatures is shown in FIGS. 17 and 18.

From luminescence during heating in FIG. 17, it is observed that a comparative mononuclear complex Eu(hfa)$_3$(TPPO)$_2$ stopped producing luminescence at 200° C. and was burnt at 250° C. The organic substance was burnt and thus even after cooling, the function as a luminescent material could not be restored.

Turning now to two complexes which were newly synthesized. It is known from TG measurement that complex 1 has a first decomposition temperature of 260° C. Complex 1 produced luminescence up to 250° C., just below 260° C., and lost luminescence at or above the decomposition temperature. However, when complex 1 was heated to 350° C. and then cooled to room temperature, complex 1 restored the luminescence function. This is a superior point of complex 1 to conventional Eu(hfa)$_3$(TPPO)$_2$.

Further, it is known from TG measurement that complex 2 has a decomposition temperature of 450° C. If a similar theory can be applied to complex 1, it is expected that complex 2 produces luminescence up to nearly 450° C. Because the measurement upper limit of the thermometer in the present experiment was 350° C., it was confirmed in the present experiment that complex 2 produces luminescence at least up to 350° C. Complex 2 may produce luminescence at a higher temperature.

When powder complexes were observed after the experiment, Eu(hfa)$_3$(TPPO)$_2$ was charred and complex 1 was slightly burnt to be a brownish colour. Meanwhile, complex 2 was still white powder which was almost the same as the powder before the experiment. This also shows high durability to heat of complex 2.

Figure 19:
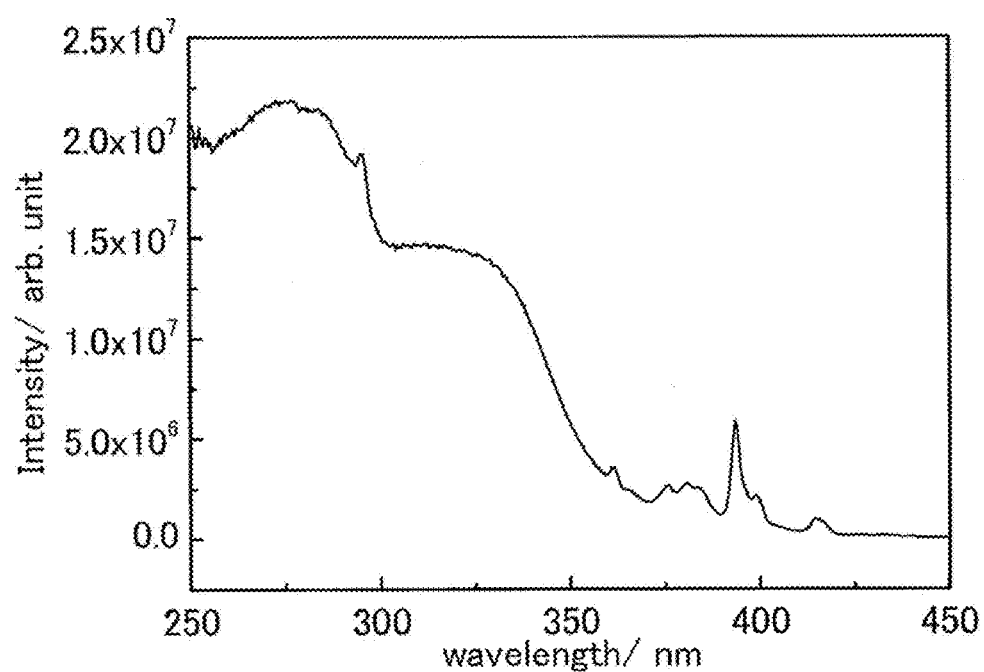
FIG. 19 shows an excitation spectrum of a thermostable Eu complex polymer (decomposition temperature: 450° C.) comprising 3 carboxylic acid moieties, and the band at 325 nm results from the photosensitizing ligand hfa and represents effective photosensitizing energy transfer.

An excitation spectrum of complex 2 (a thermostable Eu complex polymer (decomposition temperature: 450° C.) comprising three carboxylic acid moieties) is shown in FIG. 19. In the figure, the band at 325 nm results from a photosensitizing ligand hfa. From this figure, it is found that photosensitized energy transfer is effectively carried out in complex 2.

Example 4

(1) Synthesis of Eu/Tb(hfa)$_x$(TCPO)$_y$.

TCPO (0.2 mmol, 82 mg) was dissolved in methanol (2 ml) at 323 K, to which a solution of Eu(hfa)$_3$(H$_2$O)$_2$ (0.1905 mmol, 155.5 mg) and Tb(hfa)$_3$(H$_2$O)$_2$ (0.0095 mmol, 7.7 mg) in methanol (2 ml) was added. The purified precipitate was filtered, washed a few times with methanol and dried under vacuum to give a EuTb mixed complex polymer, Eu/Tb(hfa)$_x$(TCPO)$_y$ (complex 3).

Yield: 294.7 mg

ICP-AES: Eu:Tb=1.0:18.4.

(2) Properties (i) XRD

Figure 20:
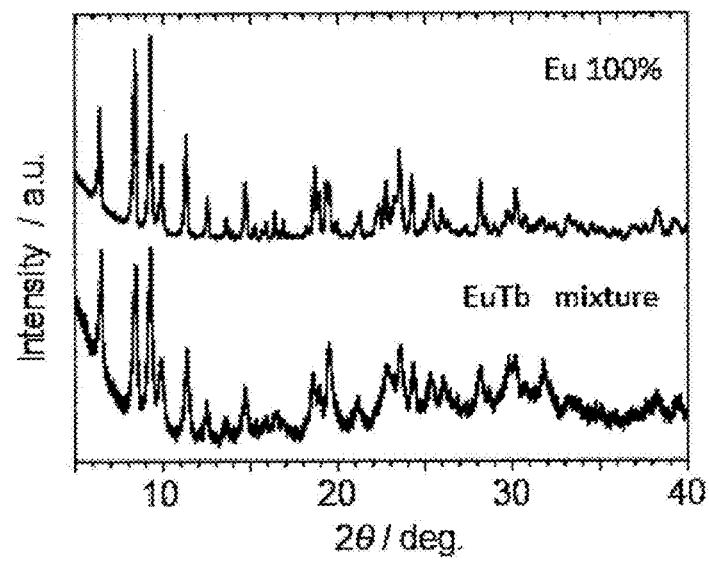
FIG. 20 shows XRD of complex 3 together with XRD of complex 2.

FIG. 20 shows XRD of complex 3. The measurement was carried out in the same manner as in Example 3.

From XRD, it is found that complex 3 has the same structure as complex 2 which comprises 100% Eu.

A predicted partial structure of complex 3 is shown below. It should be noted that the positions of Eu ions and Tb ions are not definitive and actual numbers of Eu ions and Tb ions are Eu:Tb=1.0:18.4.

[C15]

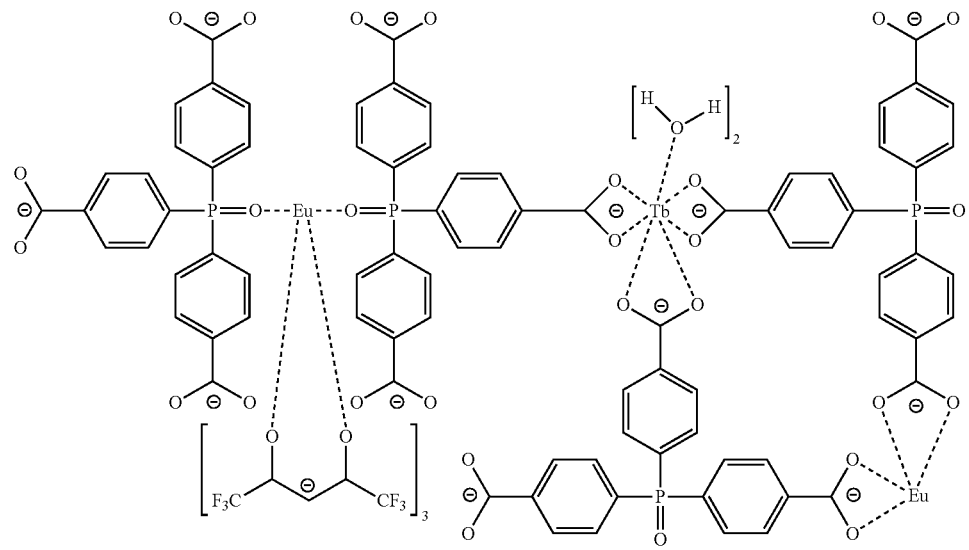

Predicted Partial Structure of Complex 3

(ii) Temperature Dependency of Luminescence

Figure 21:
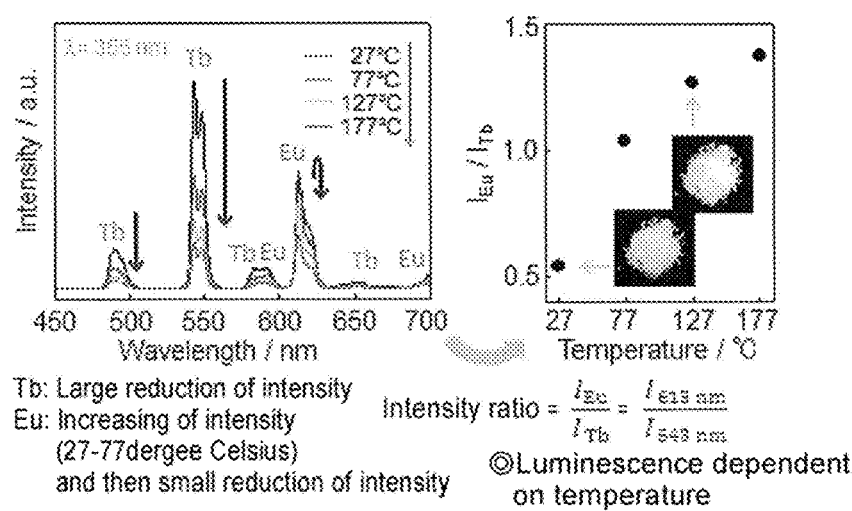
FIG. 21 shows, on left, an emission spectrum of complex 3 measured in a nitrogen atmosphere during the temperature change from 27° C. to 177° C., and, on right, a plot of the luminescence intensity of Eu relative to the luminescence intensity of Tb at respective temperatures is shown.

An emission spectrum of complex 3 measured in a nitrogen atmosphere while changing the temperature from 27° C. to 177° C. is shown on the left panel of FIG. 21. The emission spectrum was measured in the same manner as in Example 3. The peaks indicated in the figure result from luminescence from Tb and luminescence from Eu, and a peak of luminescence of Tb can be observed at around 543 nm and a peak of that of Eu at around 613 nm. On the right panel of FIG. 21, a plot of the luminescence intensity of Eu relative to that of Tb at the respective temperatures is shown. From the emission spectrum, it can be observed that the luminescence intensity of Tb significantly decreases with an increase in temperature, while a decrease in the intensity of Eu in conjunction with an increase of temperature is small and the intensity increases when the temperature is increased from 27° C. to 77° C. Because Tb and Eu respond differently to temperature, a change in the luminescent colour depending on the temperature was observed.

(iii) Excitation Spectra

Figure 22:
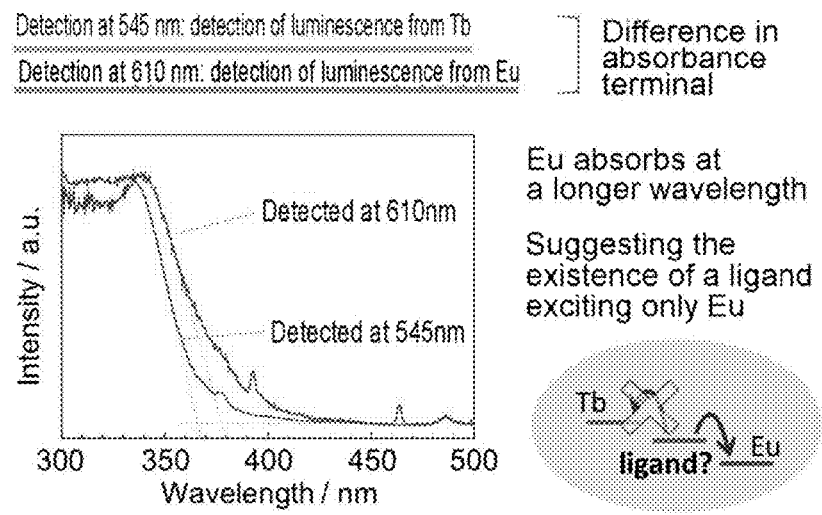
FIG. 22 shows an excitation spectrum of complex 3.
Figure 23:
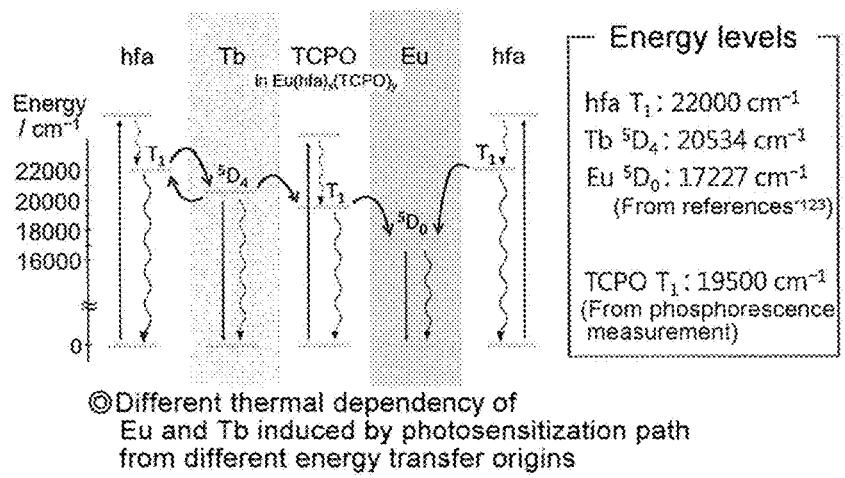
FIG. 23 shows an energy diagram estimated for complex 3.

Excitation spectra of complex 3 are shown in FIG. 22. The measurement was carried out in the same manner as in Example 3. The most notable characteristic of complex 3 is a rise of spectra which varies according to the detection wavelength in the excitation spectrum measurement. In the figure, the spectrum detected at 545 nm, which is luminescence produced from Tb, is shown in green and the spectrum detected at 610 nm, which is luminescence mainly produced from Eu, is shown in red. As the spectrum detecting Eu luminescence is observed up to longer wavelength, it is suggested that a ligand that can transfer energy only to Eu may exists. The thus predicted energy diagram is shown in FIG. 23.

(iv) Energy Diagram

The energies of hfa triplet and the levels of initiation of luminescence of Tb and Eu derive from published data, and the energy of TCPO triplet in the crystal was determined by measuring phosphorescence of a Gd complex at low temperatures. Arrows indicating possible energy transfers are added to the obtained energy levels. A hfa molecule has sufficiently high energy, and thus can provide energy to both Tb and Eu. The level of TCPO is between Tb and Eu, and thus energy transfer occurs only to Eu. Because of this, a difference in the excitation spectrum may result.

It is expected that the system in which a triplet level of a ligand exists between the levels of initiation of luminescence of Eu and Tb may contribute to a further improvement in the thermosensing capability.

INDUSTRIAL APPLICABILITY

The present invention is useful for luminescent substances and in the fields relating to luminescent substances.

The invention claimed is:

1. A coordination polymer being luminescent at a temperature equal to or higher than 250° C. and comprising a repeating unit denoted by the following general formula (10):

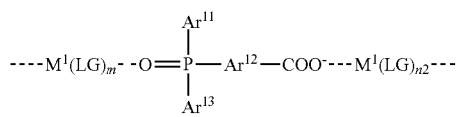

in the general formula (10):

$Ar^{11}$, $Ar^{12}$ and $Ar^{13}$ independently represent a substituted or unsubstituted aryl group, a substituted or unsubstituted heteroaryl group, or a substituted or unsubstituted aralkyl group;

$M^1$ is a rare earth element ion;

LG is a multidentate ligand coordinating with the rare earth element ion denoted by $M^1$; m and n2 are arbitrary integers of equal to or greater than 1, wherein the multidentate ligand LG is a diketonato compound;

the symbol " . . . " at the terminal of "$M^1(LG)_m$ . . . " represents a bond to a phosphine oxide group in another repeating unit;

one or both of $Ar^{11}$ and $Ar^{13}$ are unsubstituted or respectively have at least one carboxyl group and have structures denoted by the following general formulae (11) and (12); n1 and n3 are arbitrary integers of equal to or greater than 1;

the symbol " . . . " in "$M^1(LG)_m$ . . . O=P" of the general formula (10) represents a bond between $M^1$ and O=P, " . . . " in "—COO$^-$ . . . $M^1(LG)_{n2}$" represents a bond between —COO$^-$ and $M^1$; and the symbol " . . . " at the terminal of "$M^1(LG)_{n1-3}$" in the respective general formulae (10) to (12) represents a bond to a carboxyl group in another repeating unit;

and

2. The coordination polymer according to claim 1, wherein both $Ar^{11}$ and $Ar^{13}$ are unsubstituted.

3. The coordination polymer according to claim 1, wherein both $Ar^{11}$ and $Ar^{13}$ have at least one carboxyl group respectively.

4. The coordination polymer according to claim 1, wherein the diketonato compound is denoted by the general formula (3):

wherein each instance of A independently represents a hydrogen atom, a C1-6 alkyl group or a halogen atom; and Z represents a hydrogen atom or a deuterium atom.

5. The coordination polymer according to claim 4, wherein the diketonato compound is at least one compound selected from the group consisting of acetyl acetone (acac), 2,2,6,6-tetramethylheptane-3,5-dione (TMHD), 1,1,1-trifluoroacetyl acetone (TFA), 1,1,1,5,5,5-hexafluoroacetylacetone (HFA) and 1-(2-naphthyl)-4,4,4-trifluoro-1,3-butanedione.

6. The coordination polymer according to claim 1, wherein $M^1$ is at least two types of rare earth element ions.

7. A method of producing a coordination polymer, comprising a step of reacting a phosphine oxide compound denoted by the following general formula (1), a rare earth compound, provided that a rare earth ion in the rare earth compound is $M^1$, and a multidentate ligand LG which is a diketonato compound to prepare a coordination polymer being luminescent at a temperature higher than 250° C. and having a repeating unit denoted by the general formula (10) according to claim 1:

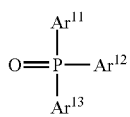 (1)

in the general formula (1):

$Ar^{11}$, $Ar^{12}$ and $Ar^{13}$ independently represent a substituted or unsubstituted aryl group, a substituted or unsubstituted heteroaryl group or a substituted or unsubstituted aralkyl group and at least one of $Ar^{11}$, $Ar^{12}$ and $Ar^{13}$ respectively has at least one carboxyl group.

8. The method according to claim 7, wherein $Ar^{11}$, $Ar^{12}$ and $Ar^{13}$ independently represent a substituted or unsubstituted aryl group and at least one of $Ar^{11}$, $Ar^{12}$ and $Ar^{13}$ respectively has at least one carboxyl group.

9. The method according to claim 7, wherein $Ar^{11}$, $Ar^{12}$ and $Ar^{13}$ independently represent a phenyl group and at least one of $Ar^{11}$, $Ar^{12}$ and $Ar^{13}$ respectively has at least one carboxyl group.

10. The coordination polymer according to claim 1, wherein $Ar^{11}$, $Ar^{12}$ and $Ar^{13}$ independently represent a phenyl group.

11. The coordination polymer according to claim 1, wherein $Ar^{11}$, $Ar^{12}$ and $Ar^{13}$ independently represent a phenyl group, $Ar^{11}$ and $Ar^{13}$ respectively is unsubstituted, $M_1$ is Eu ion, and LG is 1,1,1,5,5,5-hexafluoroacetylacetone (HFA).

12. The coordination polymer according to claim 1, wherein $Ar^{11}$, $Ar^{12}$ and $Ar^{13}$ independently represent a phenyl group, $Ar^{11}$ and $Ar^{13}$ respectively has a carboxyl group, $M_1$ is Eu ion, and LG is 1,1,1,5,5,5-hexafluoroacetylacetone (HFA).

13. The coordination polymer according to claim 1, wherein $Ar^{11}$, $Ar^{12}$ and $Ar^{13}$ independently represent a phenyl group, $Ar^{11}$ and $Ar^{13}$ respectively has a carboxyl group, $M_1$ is Eu ion and Tb ion, and LG is 1,1,1,5,5,5-hexafluoroacetylacetone (HFA).

* * * * *